United States Patent
Horsley et al.

(10) Patent No.: US 10,450,320 B2
(45) Date of Patent: Oct. 22, 2019

(54) HEXAHYDROPYRAZINOTRIAZINONE DERIVATIVES AS KINASE INHIBITORS

(71) Applicants: UCB Biopharma SPRL, Brussels (BE); Katholieke Universiteit Leuven, Leuven (BE)

(72) Inventors: Helen Tracey Horsley, Slough (GB); Richard John Mears, Abingdon (GB); Judi Charlotte Neuss, Slough (GB); James Thomas Reuberson, Slough (GB)

(73) Assignees: UCB Biopharma SPRL, Brussels (BE); Katholieke Universiteit Leuven, K.U.Leuven R&D, Leuven (BE)

(*) Notice: Subject to any disclaimer, the term of this patent is extended or adjusted under 35 U.S.C. 154(b) by 0 days.

(21) Appl. No.: 16/060,486

(22) PCT Filed: Dec. 8, 2016

(86) PCT No.: PCT/EP2016/080168
§ 371 (c)(1),
(2) Date: Jun. 8, 2018

(87) PCT Pub. No.: WO2017/097871
PCT Pub. Date: Jun. 15, 2017

(65) Prior Publication Data
US 2018/0362532 A1    Dec. 20, 2018

(30) Foreign Application Priority Data
Dec. 10, 2015 (GB) .................................. 1521767.2

(51) Int. Cl.
| *C07D 487/04* | (2006.01) |
| *A61K 31/4985* | (2006.01) |
| *A61P 31/12* | (2006.01) |
| *A61P 37/06* | (2006.01) |
| *A61P 33/06* | (2006.01) |
| *A61P 29/00* | (2006.01) |
| *A61P 35/00* | (2006.01) |
| *C07D 519/00* | (2006.01) |

(52) U.S. Cl.
CPC ........ *C07D 487/04* (2013.01); *A61K 31/4985* (2013.01); *A61P 29/00* (2018.01); *A61P 31/12* (2018.01); *A61P 33/06* (2018.01); *A61P 35/00* (2018.01); *A61P 37/06* (2018.01); *C07D 519/00* (2013.01)

(58) Field of Classification Search
CPC .................................................. C07D 487/04
See application file for complete search history.

(56) References Cited

FOREIGN PATENT DOCUMENTS

| WO | 2013/068458 | 5/2013 |
| WO | 2014/096423 | 6/2014 |

OTHER PUBLICATIONS

Written Opinion and International Search Report dated Jan. 19, 2017 for International Application No. PCT/EP2016/080168 filed Dec. 8, 2016, 9 pages.
Mejdrova et al., "Highly Selective Phosphatidylinositol 4-Kinase IIIβ Inhibitors and Structural Insight Into Their Mode of Action," Journal of Medicinal Chemistry, May 14, 2015, vol. 58, No. 9, 3767-3793.
International Preliminary Report on Patentability dated Jun. 12, 2018 for International Application No. PCT/EP2016/080168, 6 pages.

*Primary Examiner* — Karen Cheng
(74) *Attorney, Agent, or Firm* — McDonnell Boehnen Hulbert & Berghoff LLP

(57) ABSTRACT

A series of 1,2,6,7,9,9a-hexahydropyrazino[1,2-d][1,2,4]triazin-4-one derivatives, substituted in the 8-position by an optionally substituted fused bicyclic heteroaromatic group, and in the 3-position by a range of functional groups, being selective inhibitors of phosphatidylinositol-4-kinase IIIβ (PI4KIIIβ) activity, are beneficial in the treatment and/or prevention of various human ailments, including inflammatory, autoimmune and oncological disorders; viral diseases and malaria; and organ and cell transplant rejection.

20 Claims, No Drawings

HEXAHYDROPYRAZINOTRIAZINONE DERIVATIVES AS KINASE INHIBITORS

This application is a U.S. national phase application under 35 USC 371 of International Patent Application no. PCT/EP2016/080168, filed Dec. 8, 2016, which claims the benefit of Great Britain Application no. 1521767.2, filed Dec. 10, 2015.

The present invention relates to a class of fused bicyclic heterocyclic compounds, and to their use in therapy. More particularly, the present invention provides substituted hexahydropyrazino[1,2-d][1,2,4]triazin-4-one derivatives. These compounds are selective inhibitors of phosphatidylinositol-4-kinase IIIβ (PI4KIIIβ) activity, and are accordingly of benefit as pharmaceutical agents, especially in the treatment of adverse inflammatory, autoimmune and oncological disorders, in the treatment of viral diseases and malaria, and in the management of organ and cell transplant rejection.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/034738 discloses that inhibitors of PI4KIIIβ activity are useful as medicaments for the treatment of autoimmune and inflammatory disorders, and organ and cell transplant rejection.

WO 2010/103130 describes a family of oxazolo[5,4-d]pyrimidine, thiazolo[5,4-d]-pyrimidine, thieno[2,3-d]pyrimidine and purine derivatives that are active in a range of assays, including the Mixed Lymphocyte Reaction (MLR) test, and are stated to be effective for the treatment of immune and auto-immune disorders, and organ and cell transplant rejection. WO 2011/147753 discloses the same family of compounds as having significant antiviral activity. Furthermore, WO 2012/035423 discloses the same family of compounds as having significant anticancer activity.

WO 2013/024291, WO 2013/068458, WO 2014/053581 and WO 2014/096423, and copending patent applications PCT/EP2015/063048, PCT/EP2015/063051 and PCT/EP2015/063052 (published on 23 Dec. 2015 as WO 2015/193167, WO 2015/193168 and WO 2015/193169 respectively), describe various series of fused bicyclic heteroaromatic derivatives that are stated to be of benefit as pharmaceutical agents, especially in the treatment of adverse inflammatory, autoimmune and oncological disorders, in the treatment of viral diseases, and in the management of organ and cell transplant rejection.

Inhibitors of PI4KIIIβ have been identified as molecules with an ideal activity profile for the prevention, treatment and elimination of malaria (cf. C. W. McNamara et al., *Nature*, 2013, 504, 248-253).

None of the prior art available to date, however, discloses or suggests the precise structural class of substituted hexahydropyrazino[1,2-d][1,2,4]triazin-4-one derivatives as provided by the present invention as having activity as PI4KIIIβ inhibitors.

The compounds of the present invention are potent and selective inhibitors of PI4KIIIβ activity, inhibiting the kinase affinity of human PI4KIIIβ ($IC_{50}$) at concentrations of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for human PI4KIIIβ relative to other human kinases.

Certain compounds in accordance with the present invention are active as inhibitors when subjected to the Mixed Lymphocyte Reaction (MLR) test. The MLR test is predictive of immunosuppression or immunomodulation. Thus, when subjected to the MLR test, certain compounds of the present invention display an $IC_{50}$ value of 10 μM or less, generally of 5 μM or less, usually of 2 μM or less, typically of 1 μM or less, suitably of 500 nM or less, ideally of 100 nM or less, and preferably of 20 nM or less (again, the skilled person will appreciate that a lower $IC_{50}$ figure denotes a more active compound).

The compounds of the invention possess notable advantages in terms of their high potency, demonstrable efficacy at lower doses, and valuable pharmacokinetic and pharmacodynamic properties (including clearance and bioavailability).

The present invention provides a compound of formula (I) or an N-oxide thereof, or a pharmaceutically acceptable salt or solvate thereof:

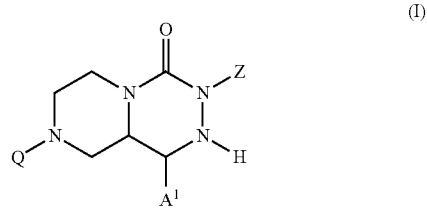

(I)

wherein

Q represents a fused bicyclic heteroaromatic group, which group may be optionally substituted by one or more substituents;

Z represents $C_{1-6}$ alkyl, $C_{2-6}$ alkenyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents; and $A^1$ represents hydrogen or trifluoromethyl; or $A^1$ represents $C_{1-6}$ alkyl, optionally substituted by one or more substituents independently selected from fluoro, hydroxy, $C_{1-6}$ alkoxy, trifluoromethoxy, amino, $C_{1-6}$ alkylamino, di($C_{1-6}$)alkylamino, carboxy, $C_{2-6}$ alkoxycarbonyl, aminocarbonyl, $C_{1-6}$ alkylaminocarbonyl and di($C_{1-6}$)alkylaminocarbonyl; or $A^1$ represents $C_{3-7}$ cycloalkyl.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl, pentyl and hexyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable $C_{2-6}$ alkenyl groups include vinyl, allyl and prop-1-en-2-yl.

Suitable $C_{3-7}$ cycloalkyl groups, which may comprise benzo-fused analogues thereof, include cyclopropyl, cyclobutyl, cyclopentyl, indanyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include oxetanyl, azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Examples of suitable heterocycloalkenyl groups include oxazolinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]-pyridinyl, pyrazolyl, pyrazolo[1,5-a]pyridinyl, pyrazolo[3,4-d]pyrimidinyl, pyrazolo[4,3-c]pyridinyl, indazolyl, oxazolyl, benzoxazolyl, isoxazolyl, benzisoxazolyl, thiazolyl, benzothiazolyl, isothiazolyl, imidazolyl, imidazo[2,1-b]thiazolyl, benzimidazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, benzothiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol ($CH=CHOH$) tautomers or amide ($NHC=O$)↔hydroxyimine ($N=COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

Typical values of the fused bicyclic heteroaromatic group Q include furo[3,2-b]-pyridinyl, furo[3,4-b]pyridinyl, furo[3,2-d]pyrimidinyl, furo[3,4-d]pyrimidinyl, thieno[2,3-b]pyridinyl, thieno[3,2-b]pyridinyl, thieno[3,4-b]pyridinyl, thieno[2,3-d]pyrimidinyl, thieno[3,2-d]pyrimidinyl, thieno[3,4-d]pyrimidinyl, pyrrolo[3,2-b]pyridinyl, pyrrolo[3,4-b]pyridinyl, pyrrolo[1,2-a]pyrimidinyl, pyrrolo[3,2-d]pyrimidinyl, pyrrolo[3,4-d]-pyrimidinyl, pyrrolo[1,2-a][1,3,5]triazinyl, pyrazolo[3,4-b]pyridinyl, pyrazolo[4,3-b]-pyridinyl, pyrazolo[4,5-b]pyridinyl, pyrazolo[1,5-a]pyrimidinyl, pyrazolo[3,4-d]-pyrimidinyl, pyrazolo[4,3-d]pyrimidinyl, pyrazolo[4,5-d]pyrimidinyl, pyrazolo[1,5-a]-[1,3,5]triazinyl, oxazolo[5,4-b]pyridinyl, oxazolo[5,4-d]pyrimidinyl, isoxazolo[4,3-b]-pyridinyl, isoxazolo[5,4-b]pyridinyl, isoxazolo[4,5-b]pyridinyl, isoxazolo[4,3-d]-pyrimidinyl, isoxazolo[4,5-d]pyrimidinyl, isoxazolo[5,4-d]pyrimidinyl, thiazolo[5,4-b]-pyridinyl, thiazolo[5,4-d]pyrimidinyl, isothiazolo[4,3-b]pyridinyl, isothiazolo[4,5-b]-pyridinyl, isothiazolo[5,4-b]pyridinyl, isothiazolo[4,3-d]pyrimidinyl, isothiazolo[4,5-d]-pyrimidinyl, isothiazolo[5,4-d]pyrimidinyl, imidazo[4,5-b]pyridinyl, imidazo[1,5-a]-pyrimidinyl, imidazo[1,5-a][1,3,5]triazinyl, purinyl, [1,2,3]triazolo[1,5-a]pyrimidinyl and [1,2,3]triazolo[1,5-a][1,3,5]triazinyl, any of which groups may be optionally substituted by one or more substituents.

Suitable values of Q include pyrazolo[3,4-b]pyridinyl, pyrazolo[3,4-d]pyrimidinyl and isoxazolo[4,5-d]pyrimidinyl, any of which groups may be optionally substituted by one or more substituents.

Typical values of optional substituents on Q include one, two or three substituents independently selected from halogen, cyano, nitro, $C_{1-6}$ alkyl, trifluoromethyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable values of optional substituents on Q include one, two or three substituents independently selected from $C_{1-6}$ alkyl and amino.

Typical values of particular substituents on Q include one, two or three substituents independently selected from fluoro, chloro, bromo, cyano, nitro, methyl, ethyl, isopropyl, trifluoromethyl, hydroxy, hydroxymethyl, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl and dimethylaminosulfonyl.

Suitable values of particular substituents on Q include one, two or three substituents independently selected from methyl and amino.

Typically, Q represents a group of formula (Qa), (Qb), (Qc), (Qd), (Qe), (Qf) or (Qg):

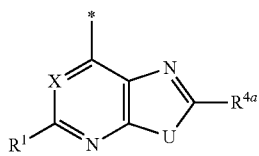
(Qa)

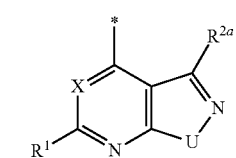
(Qb)

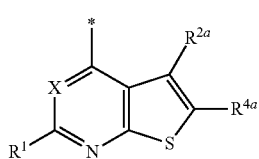
(Qc)

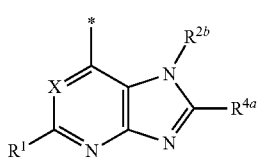
(Qd)

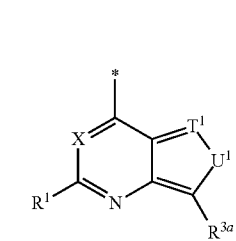
(Qe)

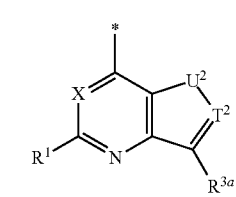
(Qf)

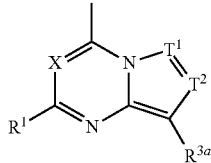
(Qg)

in which the asterisk (*) represents the point of attachment to the remainder of the molecule;

X represents N or CH;
U represents oxygen, sulfur or N—$R^{3b}$;
$U^1$ represents oxygen, sulfur or N—$R^{4b}$;
$U^2$ represents oxygen, sulfur or N—$R^{2b}$;
$T^1$ represents N or C—$R^{2a}$;
$T^2$ represents N or C—$R^{4a}$;
$R^1$ represents hydrogen, halogen, cyano, nitro, $C_{1-6}$ alkyl, trifluoromethyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^{2a}$ represents hydrogen, halogen, cyano, $C_{1-6}$ alkyl, trifluoromethyl, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^{2b}$ represents hydrogen, $C_{1-6}$ alkyl, trifluoromethyl, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^{3a}$ represents hydrogen, halogen, cyano, $C_{1-6}$ alkyl or trifluoromethyl;

$R^{3b}$ represents hydrogen or $C_{1-6}$ alkyl;

$R^{4a}$ represents hydrogen, halogen, cyano, $C_{1-6}$ alkyl, trifluoromethyl, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl; or $R^{4b}$ represents aryl or heteroaryl, either of which groups may be optionally substituted by one or more substituents; and $R^{4b}$ represents hydrogen, $C_{1-6}$ alkyl, trifluoromethyl, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl; or $R^{4b}$ represents aryl or heteroaryl, either of which groups may be optionally substituted by one or more substituents.

Suitably, Q represents a group of formula (Qb) or (Qf) as defined above.

In a first embodiment, Q represents a group of formula (Qa) as defined above. In a second embodiment, Q represents a group of formula (Qb) as defined above. In a third embodiment, Q represents a group of formula (Qc) as defined above. In a fourth embodiment, Q represents a group of formula (Qd) as defined above. In a fifth embodiment, Q represents a group of formula (Qe) as defined above. In a sixth embodiment, Q represents a group of formula (Qf) as defined above. In a seventh embodiment, Q represents a group of formula (Qg) as defined above.

In a first embodiment, X represents N. In a second embodiment, X represents CH.

In a first embodiment, U represents oxygen. In a second embodiment, U represents sulfur. In a third embodiment, U represents N—$R^{3b}$.

In a first embodiment, $U^1$ represents oxygen. In a second embodiment, $U^1$ represents sulfur. In a third embodiment, $U^1$ represents N—$R^{4b}$.

In a first embodiment, $U^2$ represents oxygen. In a second embodiment, $U^2$ represents sulfur. In a third embodiment, $U^1$ represents N—$R^{2b}$.

In a first embodiment, $T^1$ represents N. In a second embodiment, $T^1$ represents C—$R^{2a}$.

In a first embodiment, $T^2$ represents N. In a second embodiment, $T^2$ represents C—$R^{4a}$.

Typical values of $R^1$ include hydrogen, fluoro, chloro, bromo, cyano, nitro, methyl, ethyl, isopropyl, trifluoromethyl, hydroxy, hydroxymethyl, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl and dimethylaminosulfonyl.

Typically, $R^1$ represents hydrogen or amino.

In a first embodiment, $R^1$ represents hydrogen. In a second embodiment, $R^1$ represents amino.

Typical examples of particular values of $R^{2a}$ include hydrogen, fluoro, chloro, cyano, methyl, ethyl, isopropyl, trifluoromethyl, formyl, acetyl, carboxy, methoxycarbonyl, ethoxycarbonyl, aminocarbonyl, methylaminocarbonyl, dimethylaminocarbonyl, aminosulfonyl, methylaminosulfonyl and dimethylaminosulfonyl.

Suitable examples of optional values of $R^{2a}$ include hydrogen and $C_{1-6}$ alkyl.

Suitable examples of particular values of $R^{2a}$ include hydrogen and methyl.

In a first embodiment, $R^{2a}$ represents hydrogen. In a second embodiment, $R^{2a}$ represents $C_{1-6}$ alkyl, especially methyl.

Typical examples of particular values of $R^{2b}$ include hydrogen, methyl, ethyl, isopropyl, trifluoromethyl, formyl, acetyl, carboxy, methoxycarbonyl, ethoxycarbonyl, aminocarbonyl, methylaminocarbonyl, dimethylaminocarbonyl, aminosulfonyl, methylaminosulfonyl and dimethylaminosulfonyl.

Suitable examples of optional values of $R^{2b}$ include hydrogen and $C_{1-6}$ alkyl.

Suitable examples of particular values of $R^{2b}$ include hydrogen and methyl.

In a first embodiment, $R^{2b}$ represents hydrogen. In a second embodiment, $R^{2b}$ represents $C_{1-6}$ alkyl, especially methyl.

Typically, $R^{3a}$ represents hydrogen or $C_{1-6}$ alkyl.

Typical values of $R^{3a}$ include hydrogen, fluoro, chloro, cyano, methyl, ethyl and trifluoromethyl.

Suitable values of $R^{3a}$ include hydrogen and methyl.

In a first embodiment, $R^{3a}$ represents hydrogen. In a second embodiment, $R^{3a}$ represents halogen, especially fluoro or chloro. In a first aspect of that embodiment, $R^{3a}$ represents fluoro. In a second aspect of that embodiment, $R^{3a}$ represents chloro. In a third embodiment, $R^{3a}$ represents cyano. In a fourth embodiment, $R^{3a}$ represents $C_{1-6}$ alkyl, especially methyl or ethyl. In a first aspect of that embodiment, $R^{3a}$ represents methyl. In a second aspect of that embodiment, $R^{3a}$ represents ethyl. In a fifth embodiment, $R^{3a}$ represents trifluoromethyl.

Suitable values of $R^{3b}$ include hydrogen and methyl.

In a first embodiment, $R^{3b}$ represents hydrogen. In a second embodiment, $R^{3b}$ represents $C_{1-6}$ alkyl, especially methyl.

Typically, $R^{4a}$ represents hydrogen, fluoro, chloro, cyano, methyl, ethyl, isopropyl, trifluoromethyl, formyl, acetyl, carboxy, methoxycarbonyl, ethoxycarbonyl, aminocarbonyl, methylaminocarbonyl, dimethylaminocarbonyl, aminosulfonyl, methylaminosulfonyl or dimethylaminosulfonyl; or $R^{4a}$ represents phenyl, furyl or pyridinyl, any of which groups may be optionally substituted by one or more substituents.

Typical examples of optional substituents on R include one, two or three substituents independently selected from halogen, $C_{1-6}$ alkyl, trifluoromethyl, $C_{1-6}$ alkoxy and trifluoromethoxy.

Typical examples of particular substituents on $R^{4a}$ include one, two or three substituents independently selected from fluoro, chloro, bromo, methyl, trifluoromethyl, methoxy and trifluoromethoxy.

Typical examples of particular values of $R^{4a}$ include hydrogen, fluoro, chloro, cyano, methyl, ethyl, isopropyl, trifluoromethyl, formyl, acetyl, carboxy, methoxycarbonyl, ethoxycarbonyl, aminocarbonyl, methylaminocarbonyl, dimethylaminocarbonyl, aminosulfonyl, methylaminosulfonyl, dimethylaminosulfonyl, phenyl, fluorophenyl, chlorophenyl, dichlorophenyl, bromophenyl, methylphenyl, methoxyphenyl, dimethoxyphenyl, trifluoromethylphenyl, furyl and pyridinyl.

In a particular embodiment, $R^{4a}$ represents hydrogen.

Typically, $R^{4b}$ represents hydrogen, methyl, ethyl, isopropyl, trifluoromethyl, formyl, acetyl, carboxy, methoxycarbonyl, ethoxycarbonyl, aminocarbonyl, methylaminocarbonyl, dimethylaminocarbonyl, aminosulfonyl, methylaminosulfonyl or dimethylaminosulfonyl; or $R^{4b}$ represents phenyl, furyl or pyridinyl, any of which groups may be optionally substituted by one or more substituents.

Typical examples of optional substituents on $R^{4b}$ include one, two or three substituents independently selected from halogen, $C_{1-6}$ alkyl, trifluoromethyl, $C_{1-6}$ alkoxy and trifluoromethoxy.

Typical examples of particular substituents on $R^{4b}$ include one, two or three substituents independently selected from fluoro, chloro, bromo, methyl, trifluoromethyl, methoxy and trifluoromethoxy.

Typical examples of particular values of $R^{4b}$ include hydrogen, methyl, ethyl, isopropyl, trifluoromethyl, formyl, acetyl, carboxy, methoxycarbonyl, ethoxycarbonyl, aminocarbonyl, methylaminocarbonyl, dimethylaminocarbonyl, aminosulfonyl, methylaminosulfonyl, dimethylaminosulfonyl, phenyl, fluorophenyl, chlorophenyl, dichlorophenyl, bromophenyl, methylphenyl, methoxyphenyl, dimethoxyphenyl, trifluoromethylphenyl, furyl and pyridinyl.

In a particular embodiment, $R^{4b}$ represents hydrogen.

In one selected embodiment, Q represents a group of formula (Qb) as defined above wherein U represents N—$R^{3b}$. In another selected embodiment, Q represents a group of formula (Qf) as defined above wherein $U^2$ represents oxygen and $T^2$ represents N.

Typically, Z represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

Suitably, Z represents aryl or heteroaryl, either of which groups may be optionally substituted by one or more substituents.

In a first embodiment, Z represents optionally substituted $C_{1-6}$ alkyl. In a second embodiment, Z represents optionally substituted $C_{2-6}$ alkenyl. In a third embodiment, Z represents optionally substituted $C_{3-6}$ cycloalkyl. In a fourth embodiment, Z represents optionally substituted $C_{3-7}$ cycloalkyl $(C_{1-6})$alkyl. In a fifth embodiment, Z represents optionally substituted $C_{3-7}$ heterocycloalkyl. In a sixth embodiment, Z represents optionally substituted $C_{3-7}$ heterocycloalkyl $(C_{1-6})$alkyl. In a seventh embodiment, Z represents optionally substituted aryl. In an eighth embodiment, Z represents optionally substituted aryl$(C_{1-6})$alkyl. In a ninth embodiment, Z represents optionally substituted heteroaryl. In a tenth embodiment, Z represents optionally substituted heteroaryl-$(C_{1-6})$alkyl.

Typical values of Z include methyl, ethyl, isopropenyl, cyclopropyl, indanyl, cyclopropylmethyl, cyclopentylethyl, dihydrobenzofuranyl, pyrrolidinyl, indolinyl, dihydrobenzofuranylmethyl, morpholinylmethyl, morpholinylethyl, phenyl, benzyl, phenylethyl, furyl, benzofuryl, thienyl, indolyl, pyrazolyl, pyrazolo[4,3-c]pyridinyl, indazolyl, isoxazolyl, benzisoxazolyl, thiazolyl, benzothiazolyl, imidazolyl, benzimidazolyl, imidazo[1,2-a]pyridinyl, benzothiadiazolyl, benzotriazolyl, pyridinyl, quinolinyl, isoquinolinyl, pyridazinyl, pyrimidinyl, pyrazinyl, quinoxalinyl, indolylmethyl, thiazolylmethyl, imidazo[2,1-b]thiazolylmethyl, pyridinylmethyl, furylethyl, benzimidazolylethyl and pyridinylethyl, any of which groups may be optionally substituted by one or more substituents.

Suitable values of Z include phenyl and pyridinyl, either of which groups may be optionally substituted by one or more substituents.

In one embodiment, Z is unsubstituted. In another embodiment, Z is substituted by one or more substituents, typically by one, two or three substituents, suitably by one or two substituents. In one aspect of that embodiment, Z is monosubstituted. In another aspect of that embodiment, Z is disubstituted. In a further aspect of that embodiment, Z is trisubstituted.

Typical examples of optional substituents on Z include one, two or three substituents independently selected from halogen, cyano, nitro, $C_{1-6}$ alkyl, trifluoro-methyl, cyano $(C_{1-6})$alkyl, $(C_{3-7})$heterocycloalkyl, halo$(C_{3-7})$heterocycloalkyl, $(C_{1-6})$alkyl-$(C_{3-7})$heterocycloalkyl, $(C_{2-6})$alkoxycarbonyl$(C_{3-7})$heterocycloalkyl, dihalo$(C_{3-7})$-heterocycloalkyl, $(C_{3-7})$heterocycloalkyl$(C_{1-6})$alkyl, $(C_{1-6})$alkyl $(C_{3-7})$heterocycloalkyl-$(C_{1-6})$alkyl, heteroaryl, hydroxy, oxo, $C_{1-6}$ alkoxy, difluoromethoxy, trifluoromethoxy, trifluoroethoxy $(C_{3-7})$heterocycloalkoxy, $(C_{2-6})$alkoxycarbonyl $(C_{3-7})$heterocycloalkoxy, $(C_{3-7})$heterocycloalkyl$(C_{1-6})$alkoxy, aryloxy, haloaryloxy, $(C_{1-6})$alklkoxyaryloxy, $C_{1-3}$ alkylenedioxy, dihalo$(C_{1-3})$alkylenedioxy, arylcarbonyloxy, $C_{1-6}$ alkylthio, $C_{1-6}$ alkylsulfinyl, $C_{1-6}$ alkylsulfonyl, amino, $C_{1-6}$ alkylamino, di$(C_{1-6})$alkylamino, di$(C_{1-6})$alkylamino $(C_{1-6})$alkyl, arylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aryloxycarbonyl, amino-carbonyl, $C_{1-6}$ alkylaminocarbonyl, di$(C_{1-6})$ alklkylaminocarbonyl, aminosulfonyl, $C_{1-6}$ alkylaminosulfonyl and di$(C_{1-6})$alkylaminosulfonyl.

Suitable examples of optional substituents on Z include one, two or three substituents independently selected from $C_{1-6}$ alkyl, trifluoromethyl, $C_{1-6}$ alkoxy and trifluoromethoxy.

Typical examples of specific substituents on Z include one, two or three substituents independently selected from fluoro, chloro, bromo, cyano, nitro, methyl, ethyl, isopropyl, tert-butyl, trifluoromethyl, cyanomethyl, azetidinyl, pyrrolidinyl, piperazinyl, morpholinyl, fluoroazetidinyl, fluoropyrrolidinyl, methylpiperazinyl, tert-butoxycarbonylpiperazinyl, difluoroazetidinyl, difluoropyrrolidinyl, difluoropiperidinyl, pyrrolidinylmethyl, piperidinylmethyl, morpholinylmethyl, methylpiperazinylmethyl, pyrazolyl, imidazolyl, hydroxy, oxo, methoxy, ethoxy, difluoromethoxy, trifluoromethoxy, trifluoroethoxy oxetanyloxy, azetidinyloxy, tetrahydrofuranyloxy, pyrrolidinyloxy, tert-butoxycarbonylazetidinyloxy, tert-butoxycarbonylpyrrolidinyloxy, tetrahydmfuranylmethoxy, morpholinylethoxy, phenoxy, chlorophenoxy, methoxy-phenoxy, methylenedioxy, ethylenedioxy, difluoromethylenedioxy, benzoyloxy, methylthio, methylsulfinyl, methylsulfonyl, amino, methylamino, tert-butylamino, dimethylamino, dimethylaminomethyl, phenylamino, acetylamino, methoxycarbonylamino, methylsulfonylamino, formyl, acetyl, cyclopropylcarbonyl, azetidinylcarbonyl, pyrrolidinylcarbonyl, piperidinylcarbonyl, piperazinylcarbonyl, morpholinylcarbonyl, carboxy, methoxycarbonyl, ethoxycarbonyl, tert-butoxycarbonyl, benzyloxycarbonyl aminocarbonyl, methylaminocarbonyl, dimethylaminocarbonyl, aminosulfonyl, methylaminosulfonyl and dimethylaminosulfonyl.

Suitable examples of specific substituents on Z include one, two or three substituents independently selected from methyl, trifluoromethyl, methoxy and trifluoromethoxy.

Selected values of Z include phenoxymethyl, chlorophenoxymethyl, methoxyphenoxymethyl, tert-butoxycarbonylmethyl, benzyloxycarbonylmethyl, phenoxyethyl, isopropenyl, cyclopropyl, indanyl, cyclopropylmethyl, cyclopentylethyl, (methyl)(oxo)pyrrolidinyl, dihydrobenzofuranyl, methylindolinyl, dihydrobenzofuranylmethyl, morpholinylmethyl, morpholinylethyl, phenyl, nitrophenyl, methylphenyl, ethylphenyl, cyanomethylphenyl, morpholinylphenyl, pyrazolylphenyl, imidazolylphenyl, methoxyphenyl, difluoromethoxyphenyl, trifluoromethoxyphenyl, morpholinylethoxy-phenyl, ethylenedioxyphenyl, difluoromethylenedioxyphenyl, benzoyloxyphenyl, dimethylaminophenyl, acetylaminophenyl, aminocarbonylphenyl, (chloro)(methyl)-phenyl, dimethylphenyl, (methyl)(trifluoromethyl)phenyl, bis(trifluoromethyl)phenyl, (fluoropyrrolidinyl)(methyl)phenyl, (methyl)(pyrrolidinylmethyl)phenyl, (methyl)-(morpholinylmethyl)phenyl, (methyl)(methylpiperazinylmethyl)phenyl, (fluoro)-(methoxy) phenyl, (chloro)(methoxy)phenyl, (cyano)(methoxy)phenyl, (methoxy)-(methyl)phenyl, (methoxy)(trifluoromethyl)phenyl, dimethoxyphenyl, (isopropoxy)-(methyl)phenyl (difluoromethoxy)(methyl)phenyl, (methyl)(trifluoromethoxy) phenyl, (methyl)(oxetanyloxy)phenyl, (azetidinyloxy) (methyl)phenyl, (tert-butoxycarbonyl-azetidinyloxy) (methyl)phenyl, (methyl)(tetrahydrofuranylmethoxy) phenyl, (methyl)-(morpholinylethoxy)phenyl, (dimethylaminomethyl)(methyl)phenyl, trimethoxyphenyl, benzyl, cyanobenzyl, methylbenzyl, methoxybenzyl, methylenedioxybenzyl, dimethyl-aminobenzyl, dimethoxybenzyl, phenylethyl, fluorophenylethyl, methylphenylethyl, (hydroxy)(phenyl)ethyl, methoxyphenylethyl, methylfuryl, methoxybenzofuryl, thienyl, indolyl, methylindolyl, pyrazolyl, methylpyrazolyl, dimethylpyrazolyl, indazolyl, methylindazolyl, dimethylisoxazolyl, thiazolyl, methylthiazolyl, tert-butylthiazolyl, ethoxycarbonylthiazolyl, benzothiazolyl, methoxybenzothiazolyl, methylimidazolyl, benzimidazolyl, methylbenzimidazolyl, trifluoromethylbenzimidazolyl, piperidinyl-methylbenzimidazolyl, morpholinylmethylbenzimidazolyl, imidazo[1,2-a]pyridinyl, benzothiadiazolyl, pyridinyl, chloropyridinyl, methylpiperazinylpyridinyl, methoxy-pyridinyl, dimethylpyridinyl, (methyl)(trifluoromethyl)pyridinyl, (azetidinyl)(methyl)-pyridinyl, (methyl)(pyrrolidinyl)pyridinyl, (methyl)(piperazinyl)pyridinyl, (fluoro-azetidinyl)(methyl)pyridinyl, (fluoropyrrolidinyl)(methyl)pyridinyl, (methyl)(methyl-piperazinyl)pyridinyl, (tert-butoxycarbonylpiperazinyl)(methyl)pyridinyl, (difluoro-azetidinyl)(methyl)pyridinyl, (difluoropyrrolidinyl)(methyl)pyridinyl, (difluoro-piperidinyl)(methyl)pyridinyl, (methyl)pyrrolidinylmethyl)pyridinyl, (methyl)-(morpholinylmethyl)pyridinyl, (methyl)(methylpiperazinylmethyl)pyridinyl, (hydroxy)-(methyl)pyridinyl, (dimethyl)(oxo)pyridinyl, (chloro)(methoxy)pyridinyl, (methoxy)-(methyl)pyridinyl, (methoxy)(trifluoromethyl)pyridinyl, dimethoxypyridinyl, (ethoxy)-(methyl)pyridinyl, (isopropoxy)(methyl)pyridinyl, (difluoromethoxy)(methyl)pyridinyl, (methyl)(trifluoroethoxy)pyridinyl, (methyl)(tetrahydrofuranyloxy)pyridinyl, (methyl)-(pyrrolidinyloxy)pyridinyl, (tert-butoxycarbonylazetidinyloxy(methyl)pyridinyl, (tert-butoxycarbonylpyrrolidinyloxy)(methyl)pyridinyl, (methyl)(methylamino)pyridinyl, (dimethylamino)(methyl)pyridinyl, quinolinyl, isoquinolinyl, methoxypyridazinyl, pyrimidinyl, (difluoroazetidinyl)(methyl)pyrimidinyl, methoxypyrimidinyl, (methoxy)-(methyl)pyrimidinyl, (dimethylamino)(methyl)pyrimidinyl, pyrazinyl, methoxypyrazinyl, (methoxy)(methyl)pyrazinyl, (dimethylamino)(methyl)pyrazinyl, quinoxalinyl, indolylmethyl, thiazolylmethyl, methylthiazolylmethyl, imidazo[2,1-b]thiazolylmethyl, pyridinylmethyl, furylethyl, benzimidazolylethyl and pyridinylethyl.

Typical values of Z include methoxyphenyl, trifluoromethoxyphenyl, (methoxy)(methyl)phenyl and (methoxy)(trifluoromethyl)pyridinyl.

In a first embodiment, Z represents methoxyphenyl, especially 4-methoxyphenyl.

In a second embodiment, Z represents trifluoromethoxyphenyl, especially 4-(trifluoromethoxy)phenyl.

In a third embodiment, Z represents (methoxy)(methyl)phenyl, especially 4-methoxy-2-methylphenyl or 4-methoxy-3-methylphenyl. In a first aspect of that embodiment, Z represents 4-methoxy-2-methylphenyl. In a second aspect of that embodiment, Z represents 4-methoxy-3-methylphenyl.

In a fourth embodiment, Z represents (methoxy)(trifluoromethyl)pyridinyl, especially 5-methoxy-6-(trifluoromethyl)pyridinyl.

Typically, $A^1$ represents hydrogen or trifluoromethyl; or $A^1$ represents $C_{1-6}$ alkyl, optionally substituted by one or more substituents independently selected from fluoro, hydroxy and $C_{1-6}$ alkoxy.

Suitably, $A^1$ represents hydrogen or $C_{1-6}$ alkyl.

In a first embodiment, $A^1$ represents hydrogen. In a second embodiment, $A^1$ represents trifluoromethyl. In a third embodiment, $A^1$ represents $C_{1-6}$ alkyl, optionally substituted by one or more substituents independently selected from fluoro, hydroxy, $C_{1-6}$ alkoxy, trifluoromethoxy, amino, $C_{1-6}$ alkylamino, di($C_{1-6}$)alkylamino, carboxy, $C_{2-6}$ alkoxycarbonyl, aminocarbonyl, $C_{1-6}$ alkylaminocarbonyl and di($C_{1-6}$) alkylaminocarbonyl. In a first aspect of that embodiment, $A^1$ represents $C_{1-6}$ alkyl, optionally substituted by one or more substituents independently selected from hydroxy, $C_{1-6}$ alkoxy, amino, $C_{1-6}$ alkylamino, di($C_{1-6}$)alkylamino, carboxy, $C_{2-6}$ alkoxycarbonyl, amino-carbonyl, $C_{1-6}$ alkylaminocarbonyl and di($C_{1-6}$)alkylaminocarbonyl. In a second aspect of that embodiment, $A^1$ represents $C_{1-6}$ alkyl, optionally substituted by one or more substituents independently selected from hydroxy, $C_{1-6}$ alkoxy, carboxy, $C_{2-6}$ alkoxycarbonyl, aminocarbonyl, $C_{1-6}$ alkylaminocarbonyl and di($C_{1-6}$)alkylaminocarbonyl. In a third aspect of that embodiment, $A^1$ represents $C_{1-6}$ alkyl, optionally substituted by one or more substituents independently selected from hydroxy, $C_{1-6}$ alkoxy, amino, $C_{1-6}$ alkyl-amino and di($C_{1-6}$) alkylamino. In a fourth aspect of that embodiment, $A^1$ represents $C_{1-6}$ alkyl, optionally substituted by one or more substituents independently selected from fluoro, hydroxy and $C_{1-6}$ alkoxy. In a fifth aspect of that embodiment, $A^1$ represents unsubstituted $C_{1-6}$ alkyl, typically methyl, ethyl, isopropyl or isobutyl, especially methyl. In a sixth aspect of that embodiment, $A^1$ represents $C_{1-6}$ alkyl monosubstituted by hydroxy, $C_{1-6}$ alkoxy, carboxy, $C_{2-6}$ alkoxycarbonyl, aminocarbonyl, $C_{1-6}$ alkylaminocarbonyl or di($C_{1s}$)alkylaminocarbonyl. In a seventh aspect of that embodiment, $A^1$ represents $C_{1-6}$ alkyl monosubstituted by hydroxy, $C_{1-6}$ alkoxy, amino, $C_{1-6}$ alkylamino or di($C_{1-6}$)alkylamino. In an eighth aspect of that embodiment, $A^1$ represents $C_{1-6}$ alkyl disubstituted by two substituents independently selected from —$OR^a$ and —$NR^bR^c$ hydroxy, $C_{1-6}$ alkoxy, amino, $C_{1-6}$ alkylamino and di($C_{1-6}$)alkylamino. In an ninth aspect of that embodiment, $A^1$ represents $C_{1-6}$ alkyl trisubstituted by fluoro. In a fourth embodiment, $A^1$ represents $C_{3-7}$ cycloalkyl, especially cyclopropyl.

Selected values of $A^1$ include hydrogen, methyl, ethyl, isopropyl, isobutyl, trifluoromethyl, trifluoroethyl, hydroxymethyl, methoxymethyl, hydroxyethyl, methoxyethyl, carboxymethyl, methoxycarbonylmethyl, ethoxycarbonylmethyl, aminocarbonyl-methyl, dimethylaminocarbonylmethyl and cyclopropyl.

Apposite values of $A^1$ include hydrogen, methyl, ethyl, isopropyl, isobutyl, trifluoromethyl, trifluoroethyl, hydroxymethyl and hydroxyethyl.

Suitable values of $A^1$ include hydrogen and methyl.

One sub-class of compounds according to the invention is represented by the compounds of formula (IIA), and pharmaceutically acceptable salts and solvates thereof:

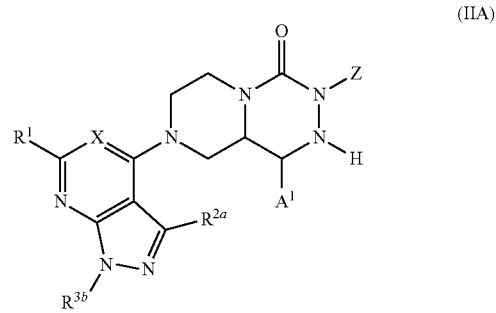

(IIA)

wherein Z, $A^1$, X, $R^1$, $R^{2a}$ and $R^{3b}$ are as defined above.

Another sub-class of compounds according to the invention is represented by the compounds of formula (IIB), and pharmaceutically acceptable salts and solvates thereof:

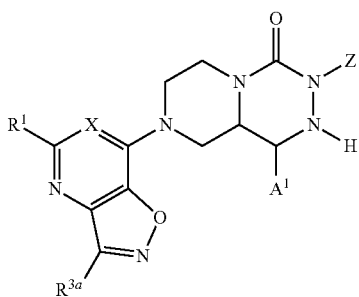

(IIB)

wherein Z, $A^1$, X, $R^1$ and $R^{3a}$ are as defined above.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments. These include inflammatory, autoimmune and oncological disorders; viral diseases and malaria; and organ and cell transplant rejection.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis and spontaneous infertility.

Oncological disorders, which may be acute or chronic, include proliferative disorders, especially cancer, in animals, including mammals, especially humans. Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

Viral diseases include infections caused by various families of virus, including the Retroviridae, Flaviviridae, Picornaviridae. Various genera within the Retroviridae family include *Alpharetrovirus, Betaretrovirus, Gammaretrovirus, Deltaretrovirus, Epsilonretrovirus, Lentivirus* and *Spumavirus*. Members of the *Lentivirus* genus include human immunodeficiency virus 1 (HIV-1) and human immunodeficiency virus 2 (HIV-2). Various genera within the Flaviviridae family include *Flavivirus, Pestivirus, Hepacivirus* and Hepatitis G Virus. Members of the Flavivirus genus include Dengue fever virus, yellow fever virus, West Nile encephalitis virus and Japanese encephalitis virus. Members of the Pestivirus genus include bovine viral diarrhoea virus (BVDV), classical swine fever virus and border disease virus 2 (BDV-2). Members of the Hepacivirus genus include hepatitis C virus (HCV). Members of the Hepatitis G Virus genus include hepatitis G virus. Various genera within the Picornaviridae family include *Aphthovirus, Avihepatovirus, Cardiovirus, Enterovirus, Erbovirus, Hepatovirus, Kobuvirus, Parechovirus, Sapelovirus, Senecavirus, Teschovirus* and *Tremovirus*. Members of the *Enterovirus* genus include poliovirus, coxsackie A virus, coxsackie B virus and rhinovirus.

Organ transplant rejection includes the rejection of transplanted or grafted organs or cells (both allografts and xenografts), including graft-versus-host reaction disease. The term "organ" as used herein means all organs or parts of organs in mammals, particularly humans, including kidney, lung, bone marrow, hair, cornea, eye (vitreous), heart, heart valve, liver, pancreas, blood vessel, skin, muscle, bone, intestine and stomach. The term "rejection" as used herein means all reactions of the recipient body or the transplanted organ which ultimately lead to cell or tissue death in the transplanted organ, or adversely affect the functional ability and viability of the transplanted organ or the recipient. In particular, this means acute and chronic rejection reactions.

Cell transplant rejection includes the rejection of cell transplants and xenotransplantation. The major hurdle for xenotransplantation is that even before the T lymphocytes (responsible for the rejection of allografts) are activated, the innate immune system (especially T-independent B lymphocytes and macrophages) is activated. This provokes two types of severe and early acute rejection, referred to as hyperacute rejection and vascular rejection respectively. Conventional immunosuppressant drugs, including cyclosporine A, are ineffective in xenotransplantation. The compounds in accordance with the present invention are not liable to this drawback. The ability of the compounds of this invention to suppress T-independent xeno-antibody production as well as macrophage activation may be demonstrated by their ability to prevent xenograft rejection in athymic, T-deficient mice receiving xenogeneic hamster-heart grafts.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

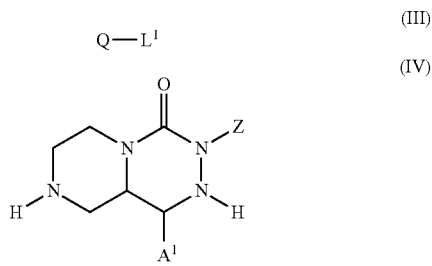

wherein Q, Z and $A^1$ are as defined above, and $L^1$ represents a suitable leaving group.

The leaving group $L^1$ is typically a halogen atom, e.g. chloro.

The reaction will generally be carried out in the presence of a base, typically an organic amine such as N,N-diisopropylethylamine. The reaction is conveniently effected at ambient or elevated temperature in a suitable solvent, e.g. a cyclic ether solvent such as tetrahydrofuran or 1,4-dioxane, or a dipolar aprotic solvent such as N,N-dimethyl-formamide, or a $C_{1-6}$ alkanol such as n-butanol, 2-propanol or ethanol.

In another procedure, the compounds of formula (I) above wherein Q represents a group of formula (Qb) in which U represents $N-R^{3b}$ may be prepared by a process which comprises reacting a compound of formula (V) with a compound of formula (VI):

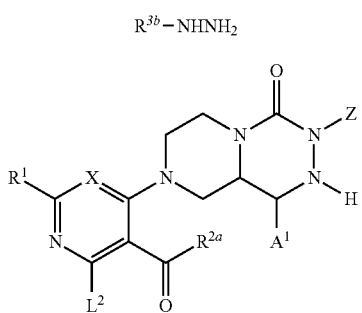

(V)

(VI)

wherein Z, $A^1$, X, $R^1$, $R^{2a}$ and $R^{3b}$ are as defined above, and $L^2$ represents a suitable leaving group.

The leaving group $L^2$ is typically a halogen atom, e.g. chloro.

The reaction is conveniently effected at an elevated temperature in a suitable solvent, e.g. an organic sulfoxide such as dimethyl sulfoxide.

The intermediates of formula (VI) above may be prepared by reacting a compound of formula (IV) as defined above with a compound of formula (VII):

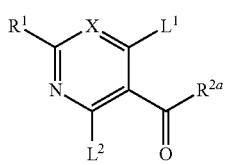

(VII)

wherein X, $R^1$, $R^2$, $L^1$ and $L^2$ are as defined above; under conditions analogous to those described above for the reaction between compounds (III) and (IV).

The intermediates of formula (IV) above may be prepared by cyclising a compound of formula (VIII):

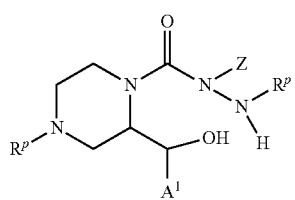

(VIII)

wherein Z and $A^1$ are as defined above, and $R^p$ represents an N-protecting group; followed by removal of the N-protecting groups $R^p$.

The N-protecting group $R^p$ is typically tert-butoxycarbonyl (BOC).

Cyclisation of compound (VIII) is suitably accomplished by treatment with triphenylphosphine and diethyl azodicarboxylate. The reaction is conveniently effected at ambient temperature in a suitable solvent, e.g. a cyclic ether solvent such as tetrahydrofuran.

Where the N-protecting group $R^p$ is BOC, subsequent removal of the BOC group may typically be accomplished by treatment with an acid, e.g. a mineral acid such as hydrochloric acid, or an organic acid such as trifluoroacetic acid. Alternatively, the BOC group may be removed by treatment with trimethylsilyl trifluoromethanesulfonate and 2,6-lutidine, typically at ambient temperature in a suitable solvent, e.g. a chlorinated solvent such as dichloromethane.

The intermediates of formula (VIII) above may be prepared by a two-step procedure which comprises: (i) reacting a compound of formula (IX):

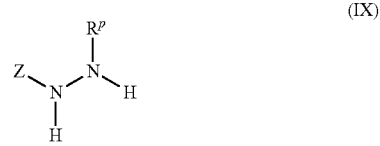

(IX)

wherein Z and $R^p$ are as defined above; with phosgene; and (ii) reacting the material thereby obtained with a compound of formula (X):

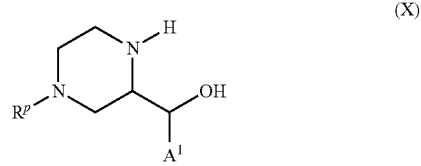

(X)

wherein $A^1$ and $R^p$ are as defined above.

Steps (i) and (ii) of the above procedure will generally be carried out in the presence of a base, typically an organic amine such as N,N-diisopropylethylamine. The reaction is conveniently effected at ambient temperature in a suitable solvent, e.g. a cyclic ether solvent such as tetrahydrofuran.

Where they are not commercially available, the starting materials of formula (III), (V), (VII), (IX) and (X) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) comprising a N—BOC moiety may be converted into the corresponding compound comprising a N—H moiety by treatment with an acid, e.g. a mineral acid such as hydrochloric acid, or an organic acid such as trifluoroacetic acid.

A compound wherein $R^1$ represents $C_{1-6}$ alkylthio, e.g. methylthio, may be converted into the corresponding compound wherein $R^1$ represents $C_{1-6}$ alkylsulfonyl, e.g. methylsulfonyl, by treatment with an oxidising agent, typically 3-chloroperoxybenzoic acid (MCPBA).

A compound wherein $R^1$ represents $C_{1-6}$ alkylsulfonyl, e.g. methylsulfonyl, may be converted into the corresponding compound wherein $R^1$ represents $C_{1-6}$ alkoxy by treatment with the appropriate sodium alkoxide salt. Similarly, a compound wherein $R^1$ represents $C_{1-6}$ alkylsulfonyl, e.g. methylsulfonyl, may be converted into the corresponding compound wherein $R^1$ represents cyano by treatment with a cyanide salt, e.g. an alkali metal cyanide salt such as sodium cyanide. Likewise, a compound wherein $R^1$ represents $C_{1-6}$ alkylsulfonyl, e.g. methylsulfonyl, may be converted into the corresponding compound wherein $R^1$ represents $C_{1-6}$ alkylamino or di($C_{1-6}$)alkylamino by treatment with the appropriate $C_{1-6}$ alkylamine or di($C_{1-6}$)alkylamine.

A compound wherein $R^{2a}$ represents $C_{2-6}$ alkoxycarbonyl may be converted into the corresponding compound wherein $R^{2a}$ represents carboxy (—$CO_2H$) by treatment with a base, typically an alkali metal hydroxide such as sodium hydroxide. A compound wherein $R^{2a}$ represents carboxy (—$CO_2H$) may be converted into the corresponding compound wherein $R^{2a}$ represents $C_{1-6}$ alkylaminocarbonyl or di($C_{1-6}$)alkylaminocarbonyl by treatment with the appropriate $C_{1-6}$ alkylamine or di($C_{1-6}$)alkylamine respectively, typically in the presence of a coupling agent such as 1-(3-dimethylaminopropyl)-3-ethyl-carbodiimide hydrochloride (EDCI) and an additive such as 1-hydroxybenzotriazole hydrate (HOBT), optionally in the presence of a base, e.g. an organic base such as N,N-diisopropylethylamine.

A compound wherein $R^{2a}$ represents carboxy (—$CO_2H$) may be converted into the corresponding compound wherein $R^{2a}$ represents aminocarbonyl (—$CONH_2$) by treatment with ammonium chloride, typically in the presence of a coupling agent such as EDCI and an additive such as HOBT, suitably in the presence of a base, e.g. an organic base such as diisopropylamine or N,N-diisopropylethylamine.

A compound wherein U represents N—$R^{3b}$ and $R^{3b}$ represents hydrogen may be converted into the corresponding compound wherein $R^{3b}$ represents $C_{1-6}$ alkyl, e.g. methyl, by treatment with a $C_{1-6}$ alkyl halide, e.g. iodomethane, usually in the presence of a base, suitably a strong inorganic base, e.g. sodium hydride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI4KIIIβ.

PI4KIIIβ Enzyme Inhibition Assay

Procedure A

Compounds were assayed utilizing reagents from Invitrogen and Promega. Compounds were screened in 1% DMSO (final) as 3-fold serial dilutions from a starting concentration of 20 μM. The 2.5×PI4Kβ reagent, the 2.5×PI Lipid Kinase Substrate/ATP mixture and the 5× compounds were prepared in 20 mM Tris pH 7.5, 0.5 mM EGTA, 2 mM DTT, 5 mM $MgCl_2$, 0.4% Triton. The final 25 μL Kinase Reaction consisted of: 4 nM PI4Kβ, 100 μM PI Lipid Kinase Substrate (both Invitrogen), and compound. The final ATP concentration in the assay was 10 μM. The detection reagents consisted of ADP-Go™ Reagent and ADP-Go™ Detect Reagent (Promega).

Briefly, compound was added to PI4Kβ followed by addition of ATP/PI Lipid Kinase Substrate mixture. The reaction mixture was incubated for 60 minutes at room temperature. The ADP-Glo™ Reagent was added and the plate was incubated for 40 minutes at room temperature, followed by addition of ADP-Go™ Detect Reagent. The plate was incubated for a further 120 minutes and read on a Luminescence plate reader. The data was fitted with XLfit from IDBS using model number 205.

Procedure B

Compounds were assayed using a PI4Kbeta Adapta assay. Compounds were screened in 1% DMSO (final) as 3-fold serial dilutions from a starting concentration of 10 μM. The 2× PI4 KB (PI4K beta)/PI Lipid Kinase Substrate mixture was prepared in 50 mM HEPES pH 7.5, 0.1% CHAPS, 1 mM EGTA, 4 mM $MgCl_2$. The final 10 μL Kinase Reaction consisted of 7.5-60 ng PI4Kβ, and 100 μM PI Lipid Kinase Substrate in 32.5 mM HEPES pH 7.5, 0.05% CHAPS, 0.5 mM EGTA, 2 mM $MgCl_2$. The final ATP concentration in the assay was 10 μM. The detection mix consisted of EDTA (30 mM), Eu-anti-ADP antibody (6 nM) and ADP tracer. The detection mix contained the EC60 concentration of tracer for 5-150 μM ATP.

Briefly, ATP was added to compound, followed by addition of a PI4Kβ/PI Lipid Kinase Substrate mixture. The plate was shaken for 30 seconds to mix, then briefly centrifuged. The reaction mixture was incubated for 60 minutes at room temperature. The detection mix was added, then the plate was shaken and centrifuged. The plate was incubated for 60 minutes at room temperature and read on a fluorescence plate reader. The data was fitted with XLfit from IDBS using model number 205.

When tested in the above assay (Procedure A or Procedure B), the compounds of the accompanying Examples were all found to possess $IC_{50}$ values for inhibition of the activity of human PI4KIIIβ of 50 μM or better.

Certain compounds in accordance with this invention are potent inhibitors when measured in the MLR test described below.

The Mixed Lymphocyte Reaction (MLR) Test

Human peripheral blood mononuclear cells (PBMCs) were isolated from buffy coats, obtained from healthy blood donors by Ficoll (Lymphoprep, Axis-Shield PoC AS, Oslo, Norway) density-gradient centrifugation. The cells at the Ficoll-plasma interface were washed three times and used as "Responder" cells. RPMI 1788 (ATCC, No CCL-156) cells were treated with mitomycin C (Kyowa, Nycomed, Brussels, Belgium) and used as "Stimulator" cells. Responder cells (0.12×106), Stimulator cells (0.045×106) and compounds (in different concentrations) were cocultured for 6 days in RPMI 1640 medium (BioWhittaker, Lonza, Belgium) supplemented with 10% fetal calf serum, 100 U/ml Geneticin (Gibco, LifeTechnologies, UK). Cells were cultured in triplicate in flat-bottomed 96-well microtiter tissue culture plates (TTP, Switzerland). After 5 days, cells were pulsed with 1 μCi of methyl-$^3$H thymidine (MP Biomedicals, USA), harvested 18 h later on glass filter paper and counted. Proliferation values were expressed as counts per minute (cpm), and converted to % inhibition with respect to a blank MLR test (identical but without added compound). The $IC_{50}$ was determined from a graph with at least four points, each derived from the mean of 2 experiments. The $IC_{50}$ value represents the lowest concentration of test compound (expressed in μM) that resulted in a 50% inhibition of the MLR.

Certain compounds of the accompanying Examples were found to generate $IC_{50}$ values in the MLR test of 10 μM or better.

EXAMPLES

| Abbreviations | |
|---|---|
| THF: tetrahydrofuran | MeOH: methanol |
| DMF: N,N-dimethylformamide | DMSO: dimethyl sulfoxide |
| DCM: dichloromethane | DIPEA: N,N-diisopropylethylamine |
| EtOH: ethanol | EtOAc: ethyl acetate |
| DEAD: diethyl azodicarboxylate | DMAP: 4-(dimethylamino)pyridine |
| IPA: isopropyl alcohol | HOBT: 1-hydroxybenzotriazole |
| EDCI: 1-(3-dimethylaminopropyl)-3-ethylcarbodiimide hydrochloride | ee: enantiomeric excess |
| | M: mass |
| h: hour | r.t.: room temperature |
| MS: Mass Spectrometry | |
| RT: retention time | |
| LCMS: Liquid Chromatography Mass Spectrometry | |
| HPLC: High Performance Liquid Chromatography | |
| ES+: Electrospray Positive Ionisation | |

Analytical and Purification Methods
Method 1
Low pH
Column: Phenomenex Kinetex-XB C18 (2.1×100 mm, 1.7 μm column)
Flow rate: 0.6 mL/minute
Solvent A: 0.1% formic acid/water
Solvent B: 0.1% formic acid/acetonitrile
Injection volume: 3 μL
Column temperature: 40° C.
UV detection wavelength: 215 nm
Eluent: 0 to 5.3 minutes: constant gradient from 95% solvent A+5% solvent B to 100% solvent B; 5.3 to 5.8 minutes: 100% solvent B; 5.80 to 5.82 minutes: constant gradient from 100% solvent B to 95% solvent A+5% solvent B.
MS detection using Waters LCT or LCT Premier, or ZQ or ZMD
UV detection using Waters 2996 photodiode array or Waters 2787 UV or Waters 2788 UV
Method 2
High pH (approximately pH 10)
Column: Phenomenex Gemini®-NX C18, 2.0×50 mm, 3 mm
Flow rate: 1 mL/minute
Solvent A: 2 nM ammonium bicarbonate, buffered to pH 10
Solvent B: acetonitrile
Injection volume: 3 μL
Column temperature: 40° C.
UV detection wavelength: 215 nm
Eluent: 0 to 1.8 minutes: constant gradient from 99% solvent A+1% solvent B to 100% solvent B; 1.8 to 2.1 minutes: 100% solvent B; 2.1 to 5.3 minutes: constant gradient from 100% solvent B to 99% solvent A+1% solvent B; 2.3 to 3.5 minutes: 99% solvent A+1% solvent B.
Method 3
Low pH
Column: Supelco Ascentis® Express C18, 2.1×30 mm, 2.7 mm
Flow rate: 1 mL/minute
Solvent A: 0.1% formic acid/water
Solvent B: 0.1% formic acid/acetonitrile
Injection volume: 3 μL
Column temperature: 40° C.
UV detection wavelength: 215 nm
Eluent: 0 to 1.5 minutes: constant gradient from 95% solvent A+5% solvent B to 100% solvent B; 1.5 to 1.6 minutes: 100% solvent B; 1.6 to 1.61 minutes: constant gradient from 100% solvent B to 95% solvent A+5% solvent B.
Method 4
High pH (approximately pH 9.5)
Column: Waters XBridge, C18, 2.1×20 mm, 2.5 μm
Solvent A: 10 mM ammonium formate in water+0.1% ammonia solution
Solvent B: acetonitrile+5% solvent A+0.1% ammonia solution
Gradient Program:

| Time | A % | B % |
|---|---|---|
| 0.00 | 95.0 | 5.0 |
| 1.50 | 5.0 | 95.0 |
| 2.50 | 5.0 | 95.0 |
| 3.00 | 95.0 | 5.0 |

Method 5
High pH (approximately pH 9.5)
Column: Waters XBridge, C18, 2.1×20 mm, 2.5 μm
Solvent A: 10 mM ammonium formate in water+0.1% ammonia solution
Solvent B: acetonitrile+5% solvent A+0.1% ammonia solution
Gradient Program:

| Time | A % | B % |
|---|---|---|
| 0.00 | 95.0 | 5.0 |
| 4.00 | 5.0 | 95.0 |
| 5.00 | 5.0 | 95.0 |
| 5.10 | 95.0 | 5.0 |

Method 6
Low pH
Column: Sunfire C18, 3.5 μm, 4.6×100 mm
Temperature: 45° C.
Flow rate: 1.9 mL/minute
Solvent A: water
Solvent B: acetonitrile
Solvent C: water+0.5% formic acid Gradient Program:

| Time | A % | B % | C % |
|------|-----|-----|-----|
| 0.00 | 85.0 | 5.0 | 10.0 |
| 5.50 | 0.0 | 90.0 | 10.0 |
| 8.00 | 0.0 | 90.0 | 10.0 |
| 8.05 | 85.0 | 5.0 | 10.0 |
| 9.90 | 85.0 | 5.0 | 10.0 |

Method 7
High pH
Column: Acquity uPLCr HSS T3, C18, 1.8 μm, 2.1×100 mm
Temperature: 45° C.
Flow rate: 0.4 mL/minute
Solvent A: water/acetonitrile/ammonium formate (95/5/63 mg/L)
Solvent B: acetonitrile
Gradient Program:

| Time | A % | B % |
|------|-----|-----|
| 0.00 | 99.0 | 1.0 |
| 5.30 | 5.0 | 95.0 |
| 5.35 | 5.0 | 95.0 |
| 7.30 | 5.0 | 95.0 |
| 7.35 | 99.0 | 1.0 |
| 9.00 | 99.0 | 1.0 |

Method 8
Low pH
Column: Sunfire C18, 3.5 μm, 4.6×100 mm
Temperature: 45° C.
Flow rate: 1.9 mL/minute
Solvent A: water
Solvent B: acetonitrile
Solvent C: water+0.5% formic acid
Gradient Program:

| Time | A % | B % | C % |
|------|-----|-----|-----|
| 0.00 | 85.0 | 5.0 | 10.0 |
| 5.50 | 0.0 | 92.5 | 7.5 |
| 8.00 | 0.0 | 92.5 | 7.5 |
| 8.05 | 85.0 | 5.0 | 10.0 |
| 9.90 | 40.0 | 50.0 | 10.0 |

Preparative HPLC
Basic Method 1

| Column: | Waters Sunfire, C18, 30 mm × 100 mm |
|---|---|
| Flow rate: | 40 mL/minute |
| Mobile Phase A: | water + 0.2% ammonium hydroxide |
| Mobile Phase B: | acetonitrile + 0.2% ammonium hydroxide |
| Particle size: | 5 μm |
| Runtime: | 15.5 minutes |
| Method (isocratic): | T = 0 minutes: 95% A; 5% B |
| | T = 2.0 minutes: 85% A; 15% B |
| | T = 12.0 minutes: 70% A; 30% B |
| | T = 12.5 minutes: 5% A; 95% B |
| | T = 15.0 minutes: 5% A; 95% B |
| | T = 15.5 minutes: 95% A; 5% B |
| Primary wavelength (collection): | 215 nm |
| Secondary wavelength: | 254 nm |
| Equipment: | Gilson 215 Liquid Handler, 2 × Gilson 306 Pumps, Gilson 805 Manometric Module, Gilson 119 UV/Vis Dual Detector |
| Software: | Gilson Unipoint V5.11 |

Basic Method 2

| Column: | Waters XBridge, C18, 19 mm × 100 mm |
|---|---|
| Flow rate: | 20 mL/minute (19 mL/min mobile phase, plus 1 mL/min acetonitrile ACD) |
| Mobile Phase A: | 10 mM ammonium bicarbonate + 0.1% ammonium hydroxide |
| Mobile Phase B: | acetonitrile + 0.1% ammonium hydroxide |
| Particle size: | 5 μm |
| Runtime: | 15 minutes |
| Method (isocratic): | T = 0 minutes: 75% A; 25% B |
| | T = 2 minutes: 75% A; 25% B |
| | T = 11 minutes: 60% A; 40% B |
| | T = 11.3 minutes: 5% A; 95% B |
| | T = 13 minutes: 5% A; 95% B |
| | T = 13.2 minutes: 75% A, 25% B |
| UV collection range: | 230-400 nm |
| Equipment: | Waters Fractionlynx system, 2545 BGM, 2767 collection module |
| Software: | Mass Lynx V4.1 SCN737 |

Polar Organic Method
Column: HILIC 250×30 mm
Flow rate: 25 mL/minute
Mobile Phase A: tert-butyl methyl ether
Mobile Phase B: ethanol:methanol (50:50)
Particle size: 5 μm
Runtime: 50 minutes
Method (isocratic): Mobile Phase B 30%; Mobile Phase A 70%
Primary wavelength (collection): Max Plot (210-240 nm)
Secondary wavelength: 254 nm
Equipment: Shimadzu LC-8A instrument
Software: LC-Solutions Intermediate 1

4-Chloro-1,3-dimethylpyrazolo[3,4-d]pyrimidin-6-amine

Methylhydrazine (~40%, 12.9 g, ~0.11 mmol) was added dropwise to a suspension of 1-(2-amino-4,6-dichloropyrimidin-5-yl)ethanone (WO 2014/096423; 25 g, 0.12 mmol) and triethylamine (36.8 g) in THF (350 mL) at −10° C. The mixture was allowed to warm to r.t. and stirred overnight. Water (200 mL) was added to the suspension. The mixture was stirred for 10 minutes, then filtered. The solid was washed with THF (50 mL) and water (300 mL), then dried in an oven at 50° C. under nitrogen for 16 h to provide a first batch of material (8.5 g). The mother liquor was concentrated to a small volume, then filtered. The resulting solid was washed with water (2×100 mL) and dried under vacuum to give a second batch of material (12.5 g). The two batches were combined, then triturated with tert-butyl methyl ether (×2) at 50° C. The solid was collected, then dried at 50° C. for 1 h in vacuo, to afford the title compound (15 g, 60%) as a white solid. $\delta_H$ (400 MHz, DMSO-$d_6$) 7.20 (s, 2H), 3.69 (s, 3H), 2.43 (s, 3H).

Intermediate 2

5-Amino-3-methyl-4H-isoxazolo[4,5-d]pyrimidin-7-one

Methyl 4-amino-3-methylisoxazole-5-carboxylate (195 g, 1.25 mol) and chloroformamidine hydrochloride (150 g, 1.31 mol) were heated in sulfolane (781 mL) at 80° C. for 45 h. The resulting viscous dark brown solution was thermoregulated at 20° C. Aqueous NaOH solution (2M, 1876 mL, 3.75 mol) was added to the reaction mixture, which was heated at 50° C. to complete cyclisation. The resulting suspension (pH 13.2) was heated at 60° C., and became a solution. After the addition of brine (820 mL), the solution was adjusted to pH 5.5 with 2M HCl (795 mL). The resulting precipitate was cooled to 10° C. over 3 h and maintained at this temperature for 1 h. The suspension was removed by filtration, then washed with deionized water (3×390 mL), followed by drying at 50° C. in a vacuum oven, to give the title compound (150 g, 66%) as a light brown solid. $\delta_H$ (400 MHz, DMSO-$d_6$) 11.40 (br s, 1H), 6.55 (s, 2H), 2.33 (s, 3H). LCMS (ES+) 167 [M+H]$^+$, RT 2.39 minutes (method 6).

Intermediate 3

N-(3-Methyl-7-oxo-4H-isoxazolo[4,5-d]pyrimidin-5-yl)acetamide

A mixture of Intermediate 2 (150 g, 0.82 mol), 4-methylmorpholine (267 g, 2.63 mol) and DMAP (11 g, 0.09 mol) was suspended in acetonitrile (680 mL) at 70° C. Acetic anhydride (184 g, 1.81 mol) was added dropwise to the reaction mixture. Once reaction was complete, the fine suspension was added to deionized water (1110 mL) over 15 minutes. The slurry was stirred at room temperature for 1.5 h. After filtration, the solid was washed with deionized water (2×450 mL), then dried at 50° C. in a vacuum oven, to give the title compound (147 g, 86%) as a beige solid. $\delta_H$ (400 MHz, DMSO-$d_6$) 12.40 (br s, 1H), 12.00 (br s, 1H), 2.43 (s, 3H), 2.18 (s, 3H). LCMS (ES+) 209 [M+H]$^+$, RT 2.68 minutes (method 7).

Intermediate 4

N-(7-Chloro-3-methylisoxazolo[4,5-d]pyrimidin-5-yl)acetamide

A suspension of Intermediate 3 (145 g, 0.70 mol) in toluene (870 mL) and N,N-diethylaniline (166 g, 1.11 mol) was heated at 70° C. Phosphoryl chloride (320.40 g, 2.09 mol) was added, and the mixture was allowed to react for 8 h. Additional toluene (580 mL) was added to the reaction mixture, before cooling to 5° C. over 7 h. The resulting suspension was filtered. The collected solid was washed firstly with toluene (435 mL) at 5° C. and secondly with toluene (435 mL) at 20° C., followed by drying at 50° C. in a vacuum oven, to afford the title compound (131 g, 80%) as an off-white solid. $\delta_H$ (400 MHz, DMSO-$d_6$) 11.10 (s, 1H), 2.57 (s, 3H), 2.18 (s, 3H). LCMS (ES+) 227/229 [M+H]$^+$, RT 3.57 minutes (method 8).

Intermediate 5

(4-Methoxy-3-methylphenyl)hydrazine

4-Methoxy-3-methylaniline (9.88 g, 68.4 mmol) was dissolved in 2M HCl (150 mL) and cooled to 0° C. (ice-bath). A solution of sodium nitrite (4.98 g, 71.8 mmol) in water (40 mL) was added slowly dropwise, ensuring that the temperature of the reaction mixture did not rise above 5° C. The reaction mixture was stirred for 30 minutes. Into a separate flask were added sodium hydrosulfite (42 g, 205 mmol), NaOH (1.4 g, 35 mmol) and water (120 mL). The mixture was cooled to 0° C. (ice-bath). The diazonium salt mixture was transferred to a dropping funnel, then slowly added to the second flask dropwise, maintaining the temperature below 5° C. Following the addition, the flask was allowed to warm to room temperature, then the pH was adjusted to pH 8 with 50% aqueous NaOH solution. The resulting orange solution was extracted with EtOAc (3×100 mL). The combined organic extracts were washed with water (100 mL) and brine (100 mL), then dried (Na$_2$SO$_4$) and evaporated, to give the title compound (10.15 g, 97.5%) as a brown solid. $\delta_H$ (400 MHz, DMSO-$d_6$) 6.71 (d, 1H, J 8.5 Hz), 6.61 (d, 1H, J 2.8 Hz), 6.58 (dd, 1H, J 8.5, 2.8 Hz), 6.15 (br s, 1H), 3.81 (br s, 2H), 3.66 (s, 3H), 2.07 (s, 3H).

Intermediate 6

[5-Methoxy-6-(trifluoromethyl)pyridin-2-yl]hydrazine

To a solution of 6-bromo-3-methoxy-2-(trifluoromethyl)pyridine (4.0 g, 15.7 mmol) in EtOH (7 mL) was added hydrazine hydrate (30 mL). The reaction mixture was heated at 100° C. for 12 h, then concentrated in vacuo. The residue was diluted with water (50 mL) and extracted with EtOAc (2×100 mL). The organic layer was separated, dried over Na$_2$SO$_4$ and concentrated in vacuo. The resulting crude material was purified by column chromatography (5% MeOH in DCM) to afford the title compound (1.00 g, 31%) as a yellow solid. $\delta_H$ (400 MHz, DMSO-$d_6$) 7.62 (d, 1H, J 9.2 Hz), 7.44 (s, 1H), 7.03 (d, 1H, J 9.2 Hz), 4.30 (br s, 2H), 3.73 (s, 3H).

Intermediate 7 tert-Butyl N-(4-methoxyanilino)carbamate

To a solution of 4-methoxyphenylhydrazine hydrochloride (4.00 g, 22.9 mmol) in MeOH (44 mL) at 0° C. was added triethylamine (6.95 g, 69.0 mmol). After 5 minutes at 0° C., di-tert-butyl dicarbonate (5.50 g, 25.2 mmol) was added. The reaction mixture was warmed to r.t. over 10 minutes, then heated at reflux for 5 h under an atmosphere of nitrogen. The reaction mixture was concentrated in vacuo, then the residue was dissolved in EtOAc (100 mL). The organic layer was washed with water (2×20 mL) and brine (20 mL), then dried over Na$_2$SO$_4$ and filtered through Kieselguhr. The filtrate was concentrated in vacuo to furnish the title compound (5.42 g, 88%) as a brown syrup. $\delta_H$(500 MHz, DMSO-$d_6$) 8.67 (br s, 1H), 7.17 (br s, 1H), 6.72-6.77 (m, 2H), 6.58-6.65 (m, 2H), 3.65 (s, 3H), 1.39 (br s, 9H). LCMS (ES+) 261 [M+Na]$^+$, RT 1.17 minutes (method 3).

Intermediate 8 tert-Butyl N-(4-methoxy-3-methylanilino)carbamate

Prepared from Intermediate 5 according to the method described for Intermediate 7, except that the reaction was performed at r.t. overnight. The crude material was purified by flash column chromatography (gradient elution with 5-20% EtOAc/isohexane) to furnish the title compound (10.4 g, 62%) as a red/brown solid. $\delta_H$ (300 MHz, DMSO-$d_6$) 8.63 (s, 1H), 7.05-7.09 (s, 1H), 6.73 (d, 1H, J 8.6 Hz), 6.43-6.50 (m, 2H), 3.67 (s, 3H), 2.07 (s, 3H), 1.39 (s, 9H). LCMS (ES+) 253 [M+H]$^+$, RT 1.41 minutes (method 4).

Intermediate 9 tert-Butyl N-{[5-methoxy-6-(trifluoromethyl)pyridin-2-yl]amino}carbamate

Prepared from Intermediate 6 according to the method described for Intermediate 8. The crude material was purified by flash column chromatography (10% MeOH in DCM) to afford the title compound (1.00 g, 67%) as a white solid. $\delta_H$ (400 MHz, DMSO-$d_6$) 8.81 (s, 1H), 8.61 (s, 1H), 7.67 (d, 1H, J 9.1 Hz), 6.82 (d, 1H, J 9.0 Hz), 3.81 (s, 3H), 1.40 (s, 9H). MS (ESI) m/z [M+H-tBu]$^+$251.9.

Intermediate 10 tert-Butyl N-[4-(trifluoromethoxy)anilino]carbamate

Prepared from 4-(trifluoromethoxy)phenylhydrazine hydrochloride (10.6 g, 45.4 mmol) according to the method described for Intermediate 8. The title compound (11.98 g, 90%) was obtained as a yellow solid. $\delta_H$ (300 MHz, DMSO-$d_6$) 8.83 (s, 1H), 7.81 (s, 1H), 7.10-7.15 (m, 2H), 6.67-6.71 (m, 2H), 1.41 (s, 9H). LCMS (ES+) 315 [M+Na]$^+$, RT 1.54 minutes (method 4).

Intermediate 11

$O^1$-Benzyl $O^4$-tert-butyl 2-(N-methoxy-N-methylcarbamoyl)piperazine-1,4-dicarboxylate To a solution of 1-(benzyloxycarbonyl)-4-(tert-butoxycarbonyl)piperazine-2-carboxylic acid (18.0 g, 49.3 mmol) in DMF (200 mL) were added N,O-dimethyl-hydroxylamine hydrochloride (10.8 g, 111 mmol), triethylamine (20.6 mL, 148 mmol), EDCI (21.2 g, 111 mmol) and HOBT (15.0 g, 111 mmol). The reaction mixture was stirred at room temperature for 5 h, then diluted with water (100 mL) and extracted with EtOAc (2×100 mL). The organic layer was separated, dried over anhydrous Na$_2$SO$_4$ and concentrated in vacuo. The crude residue was purified by flash column chromatography (10% EtOAc in hexanes) to afford the title compound (18.0 g, 90%) as a colourless semi-solid. $\delta_H$ (400 MHz, DMSO-$d_6$) 7.28-7.39 (m, 5H), 5.00-5.14 (m, 3H), 3.75 (s, 3H), 3.47 (s, 3H), 2.80-3.20 (m, 6H), 1.35 (s, 9H). MS (ESI) m/z [M+H]$^+$ 408.00.

Intermediate 12

$O^1$-Benzyl $O^4$-tert-butyl 2-acetylpiperazine-1,4-dicarboxylate

To a solution of Intermediate 11 (6.00 g, 14.7 mmol) in diethyl ether (120 mL), maintained at 0° C., was added methylmagnesium bromide (1.6M solution in THF, 31.6 mL, 44.2 mmol). The reaction mixture was stirred at room temperature for 4 h, then cooled to 0° C. and quenched with saturated aqueous ammonium chloride solution (20 mL). The aqueous layer was extracted with EtOAc (2×100 mL), then the organic layer was separated, dried over anhydrous Na$_2$SO$_4$ and concentrated in vacuo. The crude residue was purified by flash column chromatography (2% MeOH in DCM) to afford the title compound (8.00 g, 75%) as a colourless semi-solid. $\delta_H$ (400 MHz, DMSO-$d_6$) 7.17-7.40 (m, 5H), 5.06-5.19 (m, 3H), 4.67-4.75 (m, 1H), 4.41-4.57 (m, 1H), 3.72-3.82 (m, 2H), 2.95-3.05 (m, 2H), 2.18 (s, 3H), 1.37 (s, 9H). MS (ESI) m/z [M+H]$^+$ 363.00.

Intermediate 13

$O^1$-Benzyl $O^4$-tert-butyl 2-(1-hydroxyethyl)piperazine-1,4-dicarboxylate

To a solution of Intermediate 12 (6.00 g, 16.5 mmol) in THF (60 mL) and EtOH (60 mL), maintained at 0° C., was added sodium borohydride (1.87 g, 49.6 mmol). The reaction mixture was stirred at room temperature for 4 h, then quenched with saturated aqueous sodium bicarbonate solution (10 mL) and extracted with EtOAc (2×100 mL). The organic layer was dried over anhydrous Na$_2$SO$_4$ and concentrated in vacuo. The crude residue was purified by flash column chromatography (2% MeOH in DCM) to afford the title compound (5.00 g, 83%) as a colourless semi-solid. $\delta_H$ (400 MHz, DMSO-$d_6$) 7.28-7.40 (m, 5H), 5.05-5.19 (m, 2H), 4.79 (br s, 1H), 4.49 (m, 1H), 4.19-4.31 (m, 1H), 3.70-3.92 (m, 4H), 2.70-2.90 (m, 2H), 1.40 (s, 9H), 1.20 (d, 3H, J 5.7 Hz). MS (ESI) m/z [M+H]$^+$ 365.00.

Intermediate 14 tert-Butyl 3-(1-hydroxyethyl)piperazine-1-carboxylate

To a solution of Intermediate 13 (5.00 g, 13.7 mmol) in EtOH (50 mL) was added 10% Pd/C (1.50 g). The reaction mixture was stirred at 100 psi under hydrogen for 4 h, then diluted with EtOAc (2×100 mL) and filtered through celite. The filtrate was concentrated in vacuo. The crude residue was purified by column chromatography (15% MeOH in DCM) to afford the title compound (2.50 g, 81%) as a colourless semi-solid. MS (ESI) m/z [M+H]$^+$ 231.00.

Intermediate 15 tert-Butyl 4-[N-(tert-butoxycarbonylamino)-N-(4-methoxyphenyl)carbamoyl]-3-(hydroxymethyl)piperazine-1-carboxylate Anhydrous THF (16 mL) was cooled to 0° C. under an atmosphere of nitrogen and phosgene (20% solution in toluene, 2.0 mL, 4.03 mmol) was added. A pre-mixed solution of Intermediate 7 (800 mg, 2.99 mmol) and DIPEA (521 mg, 4.03 mmol) in anhydrous THF (8 mL) was added dropwise to the phosgene solution at 0° C. The reaction mixture was warmed to r.t. for 10 minutes, then cooled to 0° C. A pre-mixed solution of racemic tert-butyl 3-(hydroxymethyl)piperazine-1-carboxylate (870 mg) and DIPEA (521 mg, 4.03 mmol) in anhydrous THF (8 mL) was added at 0° C. dropwise. Once addition was complete, the reaction mixture was warmed to r.t. over 14 h, then concentrated in vacuo. The residue was re-dissolved in EtOAc (60 mL). The organic phase was washed with 1M aqueous citric acid (2×20 mL), saturated aqueous sodium bicarbonate solution (20 mL) and brine (20 mL), then dried over Na$_2$SO$_4$ and filtered. The filtrate was adsorbed onto silica (~10 mL) in vacuo. The dry-loaded material was purified by flash column chromatography (heptane/EtOAc gradient) to furnish the title compound (1.02 g, 66%) as an off-white foam. $\delta_H$ (353K, 250 MHz, DMSO-$d_6$) 9.07 (s, 1H), 7.06-7.14 (m, 2H), 6.85-6.92 (m, 2H), 4.41 (t, 1H, J 5.1 Hz), 3.98 (m, 1H), 3.90 (dt, 1H, J 13.2, 1.8 Hz), 3.75 (s, 3H), 3.71 (d, 1H, J 12.0 Hz), 3.49 (m, 3H), 2.86-2.96 (m, 2H), 2.70-2.84 (m, 1H), 1.42 (s, 9H), 1.40 (s, 9H). LCMS (ES+) 481 [M+H]$^+$, RT 1.30 minutes (method 3).

Intermediate 16 tert-Butyl 4-[N-(tert-butoxycarbonylamino)-N-(4-methoxy-3-methylphenyl)carbamoyl]-3-(hydroxymethyl)piperazine-1-carboxylate Prepared from Intermediate 8 according to the method described for Intermediate 15. The title compound (318 mg, 53%) was obtained as a colourless oil. $\delta_H$ (400 MHz, DMSO-$d_6$) 9.48 (s, 1H), 6.92-6.95 (m, 2H), 6.83-6.88 (m, 1H), 4.74 (s, 1H), 3.89-4.00 (m, 1H), 3.76 (s, 3H), 3.73 (br s, 1H), 3.39-3.44 (m, 3H), 2.67-3.00 (m, 4H), 2.11 (s, 3H), 1.37-1.43 (m, 18H). Broad peaks (rotamers). LCMS (ES+) 495 [M+H]$^+$, RT 1.48 minutes (method 4).

Intermediate 17 tert-Butyl (3S)-4-[N-(tert-butoxycarbonylamino)-N-(4-methoxy-3-methylphenyl)-carbamoyl]-3-(hydroxymethyl)piperazine-1-carboxylate Prepared from Intermediate 8 with chirally pure (>95% ee) tert-butyl (3S)-3-(hydroxymethyl)piperazine-1-carboxylate according to the method described for Intermediate 15. The title compound (3.12 g, 80%) was isolated as a colourless oil. Analytical data matched those obtained for Intermediate 16.

Intermediate 18 tert-Butyl 4-{N-(tert-butoxycarbonylamino)-N-[5-methy-6-(trifluoromethyl)pyridin-2-yl]carbamoyl}-3-(hydroxymethyl)piperazine-1-carboxylate Prepared from Intermediate 9 according to the method described for Intermediate 15. The title compound (0.66 g, 46%) was isolated as a white solid. $\delta_H$ (400 MHz, DMSO-$d_6$) 9.58 (s, 1H), 7.81 (d, 1H, J 9.2 Hz), 7.36 (d, 1H, J 8.7 Hz), 4.36 (t, 1H, J 8.5 Hz), 3.87-4.08 (m, 2H), 3.81 (s, 3H), 3.40-3.70 (m, 3H), 2.60-2.92 (m, 4H), 1.40 (s, 18H). MS (ESI) m/z [M+H]$^+$ 550.00.

Intermediate 19 tert-Butyl (3S)-4-{N-(tert-butoxycarbonylamino)-N-[4-(trifluoromethoxy)phenyl]-carbamoyl}-3-(hydroxymethyl)piperazine-1-carboxylate Prepared from Intermediate 10 and chirally pure (>95% ee) tert-butyl (3S)-3-(hydroxymethyl)piperazine-1-carboxylate according to the method described for Intermediate 15. The title compound (0.40 g, 40%) was isolated as an off-white solid. MS (ESI) m/z [M+H-BOC]$^+$435.15.

Intermediate 20 tert-Butyl 4-[N-(tert-butoxycarbonylamino)-N-(4-methoxy-3-methylphenyl)carbamoyl]-3-(1-hydroxyethyl)piperazine-1-carboxylate Prepared from Intermediate 8 and Intermediate 14 according to the method described for Intermediate 15. The title compound (1.30 g, 64%) was isolated as a white solid. $\delta_H$ (400 MHz, DMSO-$d_6$) 9.54 (s, 1H), 6.97 (d, J 8.5 Hz, 1H), 6.90 (s, 1H), 6.83 (d, J 8.5 Hz, 1H), 4.64 (br s, 1H), 4.05-4.13 (m, 1H), 3.75 (d, J 4.8 Hz, 1H), 3.68 (s, 3H), 3.40-3.54 (m, 2H), 2.60-2.88 (m, 4H), 2.10 (s, 3H), 1.39 (s, 18H), 1.20 (d, J 6.0 Hz, 3H). MS (ESI) m/z [M+H]$^+$ 509.00.

Intermediate 21

Di-tert-butyl 3-(4-methoxyphenyl)-4-oxo-6,7,9,9a-tetrahydro-1H-pyrazino[1,2-d][1,2,4]-triazine-2,8-dicarboxylate Triphenylphosphine (2.22 g, 8.46 mmol) was added to a solution of Intermediate 15 (1.01 g, 1.97 mmol) in anhydrous THF (25 mL) under an atmosphere of nitrogen. A solution of DEAD (1.10 g, 6.35 mmol) in anhydrous THF (5 mL) was added dropwise over 4 minutes. The reaction mixture was stirred for 2 h, then adsorbed onto silica (~15 mL) in vacuo and partially purified by flash column chromatography (heptane/ethyl acetate gradient). The isolated material was dissolved in diethyl ether (60 mL), then washed with 4M aqueous sodium hydroxide solution (4×10 mL) and brine (10 mL). The organic extract was dried over Na$_2$SO$_4$, then filtered. Concentration of the filtrate in vacuo furnished the title compound (796 mg, 87%) as a colourless solid. $\delta_H$ (353K, 250 MHz, DMSO-$d_6$) 7.33-7.42 (m, 2H), 6.85-6.93 (m, 2H), 4.11-4.20 (m, 2H), 3.89-4.02 (m, 2H), 3.75 (s, 3H), 3.47-3.62 (m, 2H), 2.78 (ddd, 2H, J 9.3, 4.5, 1.7 Hz), 2.61-2.74 (m, 1H), 1.44 (s, 9H), 1.39 (s, 9H). LCMS (ES+) 463 [M+H]$^+$, RT 1.75 minutes (method 3).

Intermediate 22

Di-tert-butyl 3-(4-methoxy-3-methylphenyl)-4-oxo-6,7,9,9a-tetrahydro-1H-pyrazino[1,2-d][1,2,4]triazine-2,8-dicarboxylate Prepared from Intermediate 16 according to the method described for Intermediate 21 to give the title compound (298 mg, 97%) as a colourless oil. $\delta_H$ (353 K, 400 MHz, DMSO-$d_6$) 7.15-7.24 (m, 2H), 6.86-6.91 (m, 1H), 4.11-4.18 (m, 2H), 3.92-4.02 (m, 2H), 3.79 (s, 3H), 3.50-3.71 (m, 2H), 2.73-2.85 (m, 2H), 2.65-2.72 (m, 1H), 2.15 (s, 3H), 1.45 (s, 9H), 1.41 (s, 9H). LCMS (ES+) 477 [M+H]$^+$, RT 1.56 minutes (method 4).

Intermediate 23

Di-tert-butyl (9aS)-3-(4-methoxy-3-methylphenyl)-4-oxo-6,7,9,9a-tetrahydro-1H-pyrazino[1,2-d][1,2,4]triazine-2,8-dicarboxylate Prepared from Intermediate 17 according to the method described for Intermediate 21 to give the title compound (3.3 g, quant.) as a colourless oil. Analytical data matched those obtained for Intermediate 22.

Intermediate 24

Di-tert-butyl 3-[5-methoxy-6-(trifluoromethyl)pyridin-2-yl]-4-oxo-6,7,9,9a-tetrahydro-1H-pyrazino[1,2-d][1,2,4]triazine-2,8-dicarboxylate Prepared from Intermediate 18 according to the method described for Intermediate 21 to give the title compound (0.35 g, 56%) as a brown semi-solid. $\delta_H$ (400 MHz, DMSO-$d_6$) 7.51-7.66 (m, 2H), 4.34 (t, 2H, J 8.6 Hz), 4.02-4.20 (m, 4H), 3.91 (s, 3H), 3.50-3.70 (m, 3H), 1.40 (s, 18H). MS (ESI) m/z [M+H]$^+$ 532.00.

Intermediate 25

Di-tert-butyl (9aS)-4-oxo-3-[4-(trifluoromethoxy) phenyl]-6,7,9,9a-tetrahydro-1H-pyrazino[1,2-d][1,2,4]triazine-2,8-dicarboxylate Prepared from Intermediate 19 according to the method described for Intermediate 21 to give the title compound (0.25 g, 65%) as an off-white solid. $\delta_H$ (400 MHz, DMSO-$d_6$) 7.58 (d, 2H, J 9.3 Hz), 7.33 (d, 2H, J 8.8 Hz), 4.45 (m, 2H), 3.89-4.10 (m, 3H), 3.64 (br s, 1H), 2.77 (m, 3H), 1.42 (s, 18H). MS (ESI) m/z [M+H-(t-Bu)]$^+$ 461.00.

Intermediate 26

Di-tert-butyl 3-(4-methoxy-3-methylphenyl)-1-methyl-4-oxo-6,7,9,9a-tetrahydro-1H-pyrazino[1,2-d][1,2,4]triazine-2,8-dicarboxylate Prepared from Intermediate 20 according to the method described for Intermediate 21 to give the title compound (0.20 g, 42%) as a colourless semi-solid. $\delta_H$(400 MHz, DMSO-$d_6$) 6.90-6.98 (m, 2H), 6.80-6.86 (m, 1H), 5.18-5.20 (m, 1H), 3.98-4.28 (m, 3H), 3.75 (s, 3H), 3.30-3.60 (m, 4H), 2.10 (s, 3H), 1.40 (s, 18H), 1.20 (d, 3H, J 6.0 Hz). MS (ESI) m/z [M+H]$^+$ 491.00.

Intermediate 27

3-(4-Methoxyphenyl)-2,6,7,8,9,9a-hexahydro-1H-pyrazino[1,2-d][1,2,4]triazin-4-one Hydrochloride To a solution of Intermediate 21 (796 mg, 1.72 mmol) in 1,4-dioxane (50 mL) was added hydrogen chloride (4M solution in 1,4-dioxane, 8.6 mL, 34.2 mmol). After 20 h, the reaction mixture was concentrated in vacuo. The residue was suspended in 1,4-dioxane (5 mL), then re-concentrated in vacuo, to furnish the title compound (552 mg, 89%) as a colourless solid. $\delta_H$ (500 MHz, D$_2$O) 7.26-7.30 (m, 2H), 7.03-7.07 (m, 2H), 4.51-4.57 (m, 1H), 4.00-4.07 (m, 1H), 3.88 (s, 3H), 3.52-3.63 (m, 3H), 3.15-3.30 (m, 3H), 3.12 (t, 1H, J 12.3 Hz). LCMS (ES+) 263 [M+H]$^+$, RT 1.27 minutes (method 2).

Intermediate 28

3-(4-Methoxy-3-methylphenyl)-2,6,7,8,9,9a-hexahydro-1H-pyrazino[1,2-d][1,2,4]triazin-4-one Hydrochloride Prepared from Intermediate 22 according to the method described for Intermediate 27 to give the title compound (304 mg, quant.) as an orange solid. $\delta_H$ (400 MHz, DMSO-$d_6$) 9.40 (s, 2H), 7.21-7.24 (m, 2H), 6.80-6.83 (m, 1H), 4.37-4.43 (m, 1H), 3.78-3.87 (m, 1H), 3.74 (s, 3H), 3.28-3.40 (m, 2H), 3.19-3.24 (m, 1H), 2.99-3.08 (m, 1H), 2.76-2.98 (m, 3H), 2.11 (s, 3H). LCMS (ES+) 277 [M+H]$^+$, RT 0.99 minutes (method 4).

Intermediate 29

(9aS)-3-(4-Methoxy-3-methylphenyl)-2,6,7,8,9,9a-hexahydro-1H-pyrazino[1,2-d][1,2,4]-triazin-4-one Hydrochloride Prepared from Intermediate 23 according to the method described for Intermediate 27 to give the title compound (3.6 g, quant.) as an orange solid. Analytical data matched those obtained for Intermediate 28.

Intermediate 30

3-[5-Methoxy-6-(trifluoromethyl)pyridin-2-yl]-2,6,7,8,9,9a-hexahydro-1H-pyrazino[1,2-d][1,2,4]triazin-4-one Hydrochloride Prepared from Intermediate 24 according to the method described for Intermediate 27, except that the crude material was triturated with diethyl ether (3×10 mL) and dried in vacuo, to afford the title compound (0.18 g, 69%) as an off-white solid. $\delta_H$ (400 MHz, DMSO-$d_6$) 9.40 (br s, 2H), 7.80 (d, 1H, J 9.1 Hz), 7.64 (d, 1H, J 9.0 Hz), 4.40-4.46 (m, 1H), 3.90-4.20 (m, 4H), 3.88 (s, 3H), 3.20-3.40 (m, 2H), 2.84-3.10 (m, 2H). MS (ESI) m/z [M+H]$^+$ 332.00.

Intermediate 31

(9aS)-3-[4-(Trifluoromethoxy)phenyl]-2,6,7,8,9,9a-hexahydro-1H-pyrazino[1,2-d][1,2,4]-triazin-4-one Hydrochloride Prepared from Intermediate 25 according to the method described for Intermediate 27. The title compound (0.13 g, 85%) was obtained as an off-white solid. $\delta_H$ (400 MHz, DMSO-$d_6$) 9.60 (br s, 2H), 7.66 (d, 2H, J 9.2 Hz), 7.26 (d, 2H, J 8.8 Hz), 4.43 (d, 1H, J 13.9 Hz), 3.84-3.92 (m, 1H), 3.30-3.40 (m, 2H), 3.22-3.28 (m, 2H), 2.78-3.15 (m, 3H). MS (ESI) m/z [M+H]$^+$ 317.00.

Intermediate 32

3-(4-Methoxy-3-methylphenyl)-1-methyl-2,6,7,8,9,9a-hexahydro-1H-pyrazino[1,2-d]-[1,2,4]triazin-4-one Hydrochloride Prepared from Intermediate 26 according to the method described for Intermediate 30. The title compound (0.10 g, 85%) was obtained as an off-white solid. $\delta_H$ (400 MHz, DMSO-$d_6$) 8.98 (s, 1H), 8.80 (br s, 1H), 7.40-7.45 (m, 2H), 7.30 (d, 1H, J 6.6 Hz), 6.90 (s, 1H), 4.11-4.19 (m, 2H), 3.86 (s, 3H), 3.76 (d, 2H, J 13.5 Hz), 3.32-3.40 (m, 2H), 2.90-2.98 (m, 2H), 2.16 (s, 3H), 1.22 (d, 3H, J 6.0 Hz). MS (ESI) m/z [M+H]291.00.

Intermediate 33

4-[(9aS)-3-(4-Methoxy-3-methylphenyl)-4-oxo-1,2,6,7,9,9a-hexahydropyrazino[1,2-d]-[1,2,4]triazin-8-yl]-2-chloropyridine-3-carbaldehyde A mixture of Intermediate 29 (500 mg, 1.43 mmol), 2,4-dichloropyridine-3-carbaldehyde (252 mg, 1.43 mmol) and DIPEA (1.5 mL, 8.6 mmol) in THF (10 mL) was heated to 70° C. and stirred for 3 h, then cooled to room temperature and concentrated in vacuo. The residue was dissolved in EtOAc (20 mL) and washed with saturated aqueous sodium bicarbonate solution (2×20 mL), then dried (Na$_2$SO$_4$) and evaporated onto silica. The crude residue was purified by flash column chromatography (gradient of 80-100% EtOAc in isohexane) to afford the title compound (306 mg, 51%) as a yellow gum. $\delta_H$(400 MHz, DMSO-$d_6$) 10.23 (s, 1H), 8.16 (d, 1H, J 6.1 Hz), 7.23-7.26 (m, 2H), 7.15 (d, 1H, J 6.1 Hz), 6.80-6.83 (m, 1H), 5.87 (dd, 1H, J 9.2, 4.9 Hz), 4.21-4.26 (m, 1H), 3.75-3.69 (m, 1H), 3.74 (s, 3H), 3.57-3.62 (m, 1H), 3.46-3.51 (m, 1H), 3.32-3.35 (m, 1H), 3.07-3.14 (m, 1H), 2.99-3.08 (m, 2H), 2.81-2.89 (m, 1H), 2.11 (s, 3H). LCMS (ES+) 416 [M+H]$^+$, RT 1.28 minutes (method 4).

Intermediate 34

N-{7-[(9aS)-3-(4-Methoxy-3-methylphenyl)-4-oxo-1,2,6,7,9,9a-hexahydropyrazino[1,2-d][1,2,4]triazin-8-yl]-3-methylisoxazolo[4,5-d]pyrimidin-5-yl}acetamide A mixture of Intermediate 29 (1.3 g, 4.2 mmol), Intermediate 4 (951 mg, 4.2 mmol) and DIPEA (2.2 mL, 13 mmol) in IPA (30 mL) was stirred and heated at 80° C. under nitrogen for 2.5 h, then cooled to r.t. overnight. The reaction mixture was concentrated in vacuo. The residue was dissolved in DCM (20 mL) and washed with saturated aqueous ammonium chloride solution (20 mL) and brine (20 mL), then passed through a phase separator cartridge and evaporated. The crude residue was adsorbed onto silica and purified by flash column chromatography (gradient of 40-100% EtOAc in isohexane, then 0-10% MeOH in EtOAc). The solid residue was triturated from diethyl ether, then evaporated to dryness, to give the title compound (1.33 g, 67.9%) as a cream-coloured solid. $\delta_H$ (300 MHz, DMSO-d$_6$) 10.29 (s, 1H), 7.20-7.31 (m, 2H), 6.77-6.90 (m, 1H), 5.90 (dd, 1H, J 8.8, 5.3 Hz), 4.58-4.89 (m, 2H), 4.43 (d, 1H, J 13.1 Hz), 3.75 (s, 3H), 3.56-3.71 (m, 1H), 3.35-3.48 (m, 1H), 3.06-3.48 (m, 2H), 2.84-3.07 (m, 2H), 2.46 (s, 3H), 2.17 (s, 3H), 2.12 (s, 3H). LCMS (ES+) 467 [M+H]$^+$, RT 1.60 minutes (method 5).

Example 1

8-(6-Amino-1-methylpyrazolo[3,4-d]pyrimidin-4-yl)-3-(4-methoxyphenyl)-1,2,6,7,9,9a-hexahydropyrazino[1,2-d][1,2,4]triazin-4-one To a solution of Intermediate 27 (300 mg, 0.83 mmol) in 1-butanol (8 mL) were added 4-chloro-1-methyl-1H-pyrazolo[3,4-d]pyrimidin-6-amine (WO 2014/096423; 164 mg, 0.89 mmol) and DIPEA (694 mg, 5.37 mmol). The stirred reaction mixture was heated at 110° C. for 2.5 h. After cooling, the reaction mixture was concentrated to dryness and the residue was suspended in EtOAc (40 mL). The suspension was washed with saturated aqueous sodium bicarbonate solution (2×10 mL). A precipitate, which formed at the junction of the phases, was removed by filtration (after the second sodium bicarbonate wash), then washed with water (0.5 mL) and EtOAc (2 mL). The isolated solid was purified by preparative HPLC (basic method 1) to furnish the title compound (62 mg, 17%) as a colourless solid. $\delta_H$ (500 MHz, DMSO-d$_6$) 8.03 (s, 1H), 7.37-7.43 (m, 2H), 6.80-6.86 (m, 2H), 6.22 (s, 2H), 5.90 (dd, 1H, J 8.9, 5.4 Hz), 4.57 (br s, 1H), 4.51 (br s, 1H), 4.33 (td, 1H, J 13.1, 2.7 Hz), 3.72 (s, 3H), 3.71 (s, 3H), 3.61 (ddd, 1H, J 10.4, 7.1, 3.4 Hz), 3.43 (dt, 1H, J 13.7, 5.6 Hz), 3.18 (t, 1H, J 10.9 Hz), 3.06 (s, 1H), 3.00 (dt, 1H, J 14.7, 8.2 Hz), 2.86-2.95 (m, 1H). LCMS (ES+) 410 [M+H]$^+$, RT 1.43 minutes (method 1).

Racemic Example 1 (68 mg) was resolved by chiral preparative HPLC (column: LUX A2, 20 mm×250 mm, 5 µm; eluent: ethanol containing diethylamine modifier; flow rate: 21 mL/minute; wavelength: 220 nm) to furnish (9aR)-8-(6-amino-1-methyl-1H-pyrazolo [3,4-d]pyrimidin-4-yl)-3-(4-methoxyphenyl)-1,2,6,7,9,9a-hexahydropyrazino-[1,2-d][1,2,4]triazin-4-one and (9aS)-8-(6-amino-1-methyl-1H-pyrazolo [3,4-d]pyrimidin-4-yl)-3-(4-methoxyphenyl)-1,2,6,7,9,9a-hexahydropyrazino[1,2-d][1,2,4]triazin-4-one.

First eluting enantiomer (Isomer 1; 31 mg, ee 99%): LCMS (method 1) purity 99% [UV215]. Second eluting enantiomer (Isomer 2; 36 mg, ee 96%): LCMS (method 1) purity 100% [UV215]. $^1$H NMR and LCMS data of both isomers were identical to the racemic sample.

Example 2

8-(6-Amino-1-methylpyrazolo[3,4-d]pyrimidin-4-yl)-3-(4-methoxy-3-methylphenyl)-1,2,6,7,9,9a-hexahydropyrazino[1,2-d][1,2,4]triazin-4-one Prepared from Intermediate 28 according to the method described for Example 1, except that the EtOAc solution from the work-up was evaporated onto silica and purified by flash column chromatography (gradient of 1-10% MeOH in EtOAc). The fractions containing the product were evaporated and freeze-dried from acetonitrile/water to yield the title compound (502 mg, 21%) as a white solid. $\delta_H$ (400 MHz, DMSO-d$_6$) 8.03 (s, 1H), 7.24-7.27 (m, 2H), 6.80-6.83 (m, 1H), 6.22 (s, 2H), 5.87 (dd, 1H, J 8.8, 5.3 Hz), 4.46-4.62 (m, 2H), 4.30-4.35 (m, 1H), 3.74 (s, 3H), 3.71 (s, 3H), 3.56-3.64 (m, 1H), 3.38-3.45 (m, 1H), 3.14-3.21 (m, 1H), 2.95-3.09 (m, 2H), 2.86-2.93 (m, 1H), 2.12 (s, 3H). LCMS (ES+) 424 [M+H]$^+$, RT 1.39 minutes (method 5).

Example 3

(9aS)-8-(6-Amino-1-methyl-1H-pyrazolo[3,4-d]pyrimidin-4-yl)-3-(4-methoxy-3-methylphenyl)-1,2,6,7,9,9a-hexahydropyrazino[1,2-d][1,2,4]triazin-4-one DIPEA (3.8 mL, 22 mmol) was added to a suspension of Intermediate 29 (1.25 g, 3.58 mmol) and 4-chloro-1-methyl-1H-pyrazolo[3,4-d]pyrimidin-6-amine (WO 2014/096423; 657 mg, 3.58 mmol) in 1-butanol (40 mL). The reaction mixture was heated at 110° C. for 3.5 h, then cooled to r.t. and concentrated in vacuo. The residue was dissolved in EtOAc (20 mL) and filtered through celite (to remove some insoluble material), then washed with saturated aqueous sodium bicarbonate solution (2×20 mL) and dried over Na$_2$SO$_4$. The organic fraction was evaporated onto silica and purified by flash column chromatography (gradient of 3-10% MeOH in EtOAc). The second eluting material was triturated from EtOAc and filtered, then washed with EtOAc and isohexane. The residue was evaporated to dryness. The resulting cream-coloured solid (410 mg) was further purified by preparative HPLC (basic method 2), then freeze-dried from acetonitrile/water, to yield the title compound (44 mg, 2.9%) as a white solid. Analytical data matched those obtained for Example 2.

Example 4

(9aS)-8-(6-Amino-1-methyl-1H-pyrazolo[3,4-d]pyrimidin-4-yl)-3-(4-methoxy-3-methylphenyl)-6,7,9,9a-tetrahydropyrazino[1,2-d][1,2,4]triazin-4-one The first eluting material obtained from the reaction described in Example 3 was freeze-dried from acetonitrile/water to yield the title compound (63.2 mg, 4%) as a white solid. $\delta_H$ (400 MHz, DMSO-d$_6$) 8.11 (s, 1H), 7.13-7.17 (m, 3H), 6.91 (d, 1H, J 8.7 Hz), 6.28 (s, 2H), 4.76-4.81 (m, 1H), 4.63-4.68 (m, 1H), 4.37 (ddd, 1H, J 11.4, 3.2, 1.8 Hz), 4.18-4.23 (m, 1H), 3.80 (s, 3H), 3.73 (s, 3H), 3.14-3.33 (m, 2H), 2.88-2.95 (m, 1H), 2.15 (s, 3H). LCMS (ES+) 422 [M+H]$^+$, RT 1.64 minutes (method 5).

Example 5

8-(6-Amino-1,3-dimethylpyrazolo[3,4-d]pyrimidin-4-yl)-3-(4-methoxy-3-methylphenyl)-1,2,6,7,9,9a-hexahydropyrazino[1,2-d][1,2,4]triazin-4-one Prepared from Intermediate 28 and Intermediate 1 according to the method described for Example 2. The title compound (105 mg, 27%) was isolated as a white solid. $\delta_H$ (400 MHz, DMSO-d$_6$) 7.23-7.26 (m, 2H), 6.80-6.83 (m, 1H), 6.31 (s, 2H), 5.86 (dd, 1H, J 9.1, 5.0 Hz), 4.33-4.38 (m, 1H), 4.13-4.17 (m, 1H), 4.06-4.11 (m, 1H), 3.74 (s, 3H), 3.60-3.68 (m, 1H), 3.64 (s, 3H), 3.34-3.41 (m, 1H), 2.99-3.07 (m, 1H), 2.88-2.97 (m, 3H), 2.42 (s, 3H), 2.11 (s, 3H). LCMS (ES+) 438 [M+H]$^+$, RT 1.16 minutes (method 5).

Example 6

(9aS)-8-(6-Amino-1,3-dimethylpyrazolo[3,4-d]pyrimidin-4-yl)-3-(4-methoxy-3-methylphenyl)-1,2,6,7,9,9a-hexahydropyrazino[1,2-d][1,2,4]triazin-4-one Prepared from Intermediate 29 and Intermediate 1 according to the method described for Example 2. The title compound (76 mg, 26%, ee 94.2%) was isolated as a white solid. Analytical data matched those obtained for Example 5.

Example 7

8-(6-Amino-1-methyl-1H-pyrazolo[3,4-d]pyrimidin-4-yl)-3-[5-methoxy-6-(trifluoro-methyl)pyridin-2-yl]-1,2,6,7,9,9a-hexahydropyrazino[1,2-d][1,2,4]triazin-4-one To a solution of Intermediate 30 (0.18 g, 0.77 mmol) in EtOH (20 mL) were added DIPEA (0.38 mL, 2.33 mmol) and 4-chloro-1-methyl-1H-pyrazolo[3,4-d]-pyrimidin-6-amine (WO 2014/096423; 0.21 g, 1.16 mmol). The reaction mixture was heated at 80° C. for 4 h, then diluted with water (20 mL) and extracted with EtOAc (3×20 mL). The organic layer was separated, dried over anhydrous Na$_2$SO$_4$ and concentrated in vacuo. The crude residue was purified by flash column chromatography (5% DCM in MeOH) to afford the title compound (0.06 g, 18%) as an off-white solid. $\delta_H$ (400 MHz, DMSO-d$_6$) 8.05 (s, 1H), 7.78 (d, 1H, J 9.0 Hz), 7.68 (d, 1H, J 9.0 Hz), 6.24 (s, 2H), 6.02-6.10 (m, 1H), 4.44-4.62 (m, 2H), 4.33 (d, 1H, J 12.9 Hz), 3.92 (s, 3H), 3.71 (s, 3H), 3.60-3.68 (m, 1H), 3.40-3.50 (m, 1H), 2.95-3.24 (m, 4H). MS (ESI) m/z [M+H]$^+$ 479.00.

Example 8

(9aS)-8-(6-Amino-1-methyl-1H-pyrazolo[3,4-d]pyrimidin-4-yl)-3-[4-(trifluoromethoxy)-phenyl]-1,2,6,7,9,9a-hexahydropyrazino[1,2-d][1,2,4]triazin-4-one Prepared from Intermediate 31 according to the method described for Example 2. The title compound (0.06 g, 34%) was obtained as an off-white solid. $\delta_H$ (400 MHz, DMSO-d$_6$) 8.04 (s, 1H), 7.70 (d, 2H, J 9.19 Hz), 7.26 (d, 2H, J 8.73 Hz), 6.24 (s, 2H), 6.00 (m, 1H), 4.58 (br s, 2H), 4.36 (d, 1H, J 13.33 Hz), 3.71 (s, 3H), 3.65 (m, 1H), 3.40-3.53 (m, 1H), 3.18 (m, 1H), 2.89-3.12 (m, 3H). MS (ESI) m/z [M+H]$^+$ 464.00.

Example 9 cis- and trans-8-(6-Amino-1-methyl-1H-pyrazolo[3,4-d]pyrimidin-4-yl)-3-(4-methoxy-3-methylphenyl)-1-methyl-1,2,6,7,9,9a-hexahydropyrazino[1,2-d][1,2,4]triazin-4-one To a solution of Intermediate 32 (0.10 g, 0.34 mmol) in EtOH (10 mL) was added DIPEA (0.17 mL, 1.03 mmol), followed by 4-chloro-1-methyl-1H-pyrazolo[3,4-d]-pyrimidin-6-amine (WO 2014/096423; 0.09 g, 0.51 mmol). The reaction mixture was heated at 100° C. for 12 h, then cooled to r.t. and concentrated in vacuo. The residue was diluted with DCM (20 mL) and filtered, then the filtrate was concentrated in vacuo. The crude residue was purified by column chromatography (gradient of 0-4% MeOH in DCM) to afford the title compound as a 3:1 trans:cis isomer mixture. The two isomers were separated by HPLC (polar organic method).

The cis isomer, the first eluting peak (34 mg, 22%), was obtained as an off-white solid. LCMS (method 5) purity 97.6%. $\delta_H$ (400 MHz, DMSO-d$_6$) 7.98 (s, 1H), 7.26 (m, 2H), 6.82 (d, 1H, J 8.4 Hz), 6.24 (s, 2H), 5.72 (d, 1H, J 10.5 Hz), 4.50-4.70 (m, 2H), 4.35 (d, 1H, J 12.9 Hz), 3.74 (s, 3H), 3.70 (s, 3H), 3.20-3.30 (m, 2H), 3.05 (dd, J 17.2, 7.9 Hz, 1H), 2.92-2.81 (m, 2H), 2.12 (s, 3H), 1.25 (d, 3H, J 6.4 Hz). MS (ESI) m/z [M+H]438.00.

The trans isomer, the second eluting peak (95 mg, 64%), was obtained as an off-white solid. LCMS (method 5) purity 96.6%. $\delta_H$ (400 MHz, DMSO-d$_6$) 7.98 (s, 1H), 7.26 (m, 2H), 6.82 (d, J 8.4 Hz, 1H), 6.24 (s, 2H), 5.93 (d, 1H, J 7.6 Hz), 4.50-4.60 (m, 2H), 4.35 (d, 1H, J 12.9 Hz), 3.74 (s, 3H), 3.70 (s, 3H), 3.44-3.54 (m, 2H), 3.20-3.30 (m, 2H), 2.92-3.00 (m, 1H), 2.12 (s, 3H), 1.16 (d, 3H, J 6.4 Hz). MS (ESI) m/z [M+H]438.00.

The cis isomer (23.8 mg) was resolved by chiral preparative HPLC (column: Chiralpak AS-V, 50 mm×490 mm, 20 μm; eluent: 50% heptane and 50% ethanol containing 0.1% diethylamine modifier, flow rate: 80 mL/minute; temperature: 30° C.; wavelength: 220 nm) to furnish (1R,9aR)-8-(6-amino-1-methyl-1H-pyrazolo[3,4-d]-pyrimidin-4-yl)-3-(4-methoxy-3-methylphenyl)-1-methyl-1,2,6,7,9,9a-hexahydropyrazino[1,2-d][1,2,4]triazin-4-one and (1S,9aS)-8-(6-amino-1-methyl-1H-pyrazolo [3,4-d]pyrimidin-4-yl)-3-(4-methoxy-3-methylphenyl)-1-methyl-1,2,6,7,9,9a-hexahydropyrazino[1,2-d][1,2,4]triazin-4-one. First eluting enantiomer (Isomer 1; 10.3 mg, ee 100%): LCMS (method 5) purity 93.8%. Second eluting enantiomer (Isomer 2; 10.3 mg, ee 99.2%): LCMS (method 5) purity 96.3%. $^1$H NMR and LCMS data of both isomers were identical to the racemic sample.

The trans isomer (84 mg) was resolved by chiral preparative HPLC (column: Chiralpak AS-V, 50 mm×490 mm, 20 μm; eluent: 50% heptane and 50% ethanol containing 0.1% diethylamine modifier, flow rate: 80 mL/minute; temperature: 30° C.; wavelength: 220 nm) to furnish (S,9aR)-8-(6-amino-1-methyl-1H-pyrazolo[3,4-d]-pyrimidin-4-yl)-3-(4-methoxy-3-methylphenyl)-1-methyl-1,2,6,7,9,9a-hexahydropyrazino[1,2-d][1,2,4]triazin-4-one and (1R, 9aS)-8-(6-amino-1-methyl-1H-pyrazolo[3,4-d]pyrimidin-4-yl)-3-(4-methoxy-3-methylphenyl)-1-methyl-1,2,6,7,9,9a-hexahydropyrazino[1,2-d][1,2,4]triazin-4-one. First eluting enantiomer (Isomer 1; 36.7 mg, ee 100%): LCMS (method 5) purity 97.5%. Second eluting enantiomer (Isomer 2; 41.9 mg, ee 96.1%): LCMS (method 5) purity 99.4%. $^1$H NMR and LCMS data of both isomers were identical to the racemic sample.

Example 10

(9aS)-3-(4-Methoxy-3-methylphenyl)-8-(1-methyl-1H-pyrazolo[3,4-b]pyridin-4-yl)-1,2,6,7,9,9a-hexahydropyrazino[1,2-d][1,2,4]triazin-4-one A solution of Intermediate 33 (306 mg, 0.74 mmol) in DMSO (3 mL) was treated with methylhydrazine (0.3 mL) and heated at 150° C. under microwave irradiation for 2 h. The reaction mixture was added to water (50 mL). The resulting cloudy solution was extracted with EtOAc (3×20 mL). The combined EtOAc layers were washed with brine (20 mL), dried (Na$_2$SO$_4$) and evaporated onto silica. The crude residue was purified by flash column chromatography (gradient of 1-10% MeOH in EtOAc). After freeze-drying from acetonitrile/water, the title compound (59 mg, 20%) was obtained as a white solid. $\delta_H$ (400 MHz, DMSO-d$_6$) 8.30 (s, 1H), 8.15 (d, 1H, J 5.6 Hz), 7.25-7.28 (m, 2H), 6.81-6.84 (m, 1H), 6.49 (d, 1H, J 5.7 Hz), 5.89 (dd, 1H, J 9.0, 5.2 Hz), 4.33 (dt, 1H, J 13.0, 3.0 Hz), 4.14-4.19 (m, 1H), 4.07-4.12 (m, 1H), 3.96 (s, 3H), 3.70-3.81 (m, 1H), 3.75 (s, 3H), 3.45 (ddd, 1H, J 13.9, 5.6, 5.6 Hz), 3.16-3.24 (m, 1H), 2.95-3.13 (m, 3H), 2.13 (s, 3H). LCMS (ES+) 408 [M+H]$^+$, RT 1.52 minutes (method 5).

Example 11

(9aS)-8-(5-Amino-3-methylisoxazolo[4,5-d]pyrimidin-7-yl)-3-(4-methoxy-3-methylphenyl)-1,2,6,7,9,9a-hexahydropyrazino[1,2-d][1,2,4]triazin-4-one A solution of Intermediate 34 (1.33 g, 2.85 mmol) in MeOH (50 mL) was treated with 10% NaOH (5 mL), then heated to 65° C. and stirred for 2.5 h. A cream-coloured solid was formed. The reaction mixture was neutralised to pH 7 with 10% HCl, then filtered. The residue was washed successively with MeOH, diethyl ether and isohexane, then evaporated to dryness. The resulting cream-coloured solid was suspended in acetonitrile/water, and freeze-dried, to yield a first batch of material (915 mg) as a cream-coloured solid. The filtrate was concentrated in vacuo, and the remaining aqueous mixture was extracted with DCM (2×20 mL). The organic phases were combined and washed with brine (20 mL), then passed through a phase separator cartridge and evaporated. The resulting cream-coloured solid was triturated from EtOAc and filtered, then washed with isohexane and evaporated to dryness, to yield a second batch of material (140 mg) as a cream-coloured solid. Both batches were combined to yield the title compound (1.06 g, 87%). $\delta_H$ (300 MHz, DMSO-d$_6$) 7.20-7.31 (m, 2H), 6.75-6.86 (m, 1H), 6.25 (s, 2H), 5.88 (dd, 1H, J 8.9, 5.2 Hz), 4.65 (dd, 2H, J 26.3, 13.0 Hz), 4.41 (d, 1H, J 13.0 Hz), 3.75 (s, 3H), 3.61 (d, 1H, J 9.5 Hz), 3.40 (dt, 1H, J 14.0, 5.7 Hz), 3.03-3.25 (m, 2H), 2.81-3.03 (m, 2H), 2.36 (s, 3H), 2.12 (s, 3H). LCMS (ES+) 425 [M+H]$^+$, RT 1.61 minutes (method 5).

The invention claimed is:
1. A compound of formula (I) or an N-oxide thereof, or a pharmaceutically acceptable salt or solvate thereof:

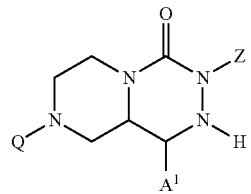

(I)

wherein
Q represents a fused bicyclic heteroaromatic group, which group may be optionally substituted by one or more substituents;
Z represents $C_{1-6}$ alkyl, $C_{2-6}$ alkenyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents; and
$A^1$ represents hydrogen or trifluoromethyl; or $A^1$ represents $C_{1-6}$ alkyl, optionally substituted by one or more substituents independently selected from fluoro, hydroxy, $C_{1-6}$ alkoxy, trifluoromethoxy, amino, $C_{1-6}$ alkylamino, di($C_{1-6}$)alkylamino, carboxy, $C_{2-6}$ alkoxycarbonyl, aminocarbonyl, $C_{1-6}$ alkylaminocarbonyl and di($C_{1-6}$)alkylaminocarbonyl; or $A^1$ represents $C_{3-7}$ cycloalkyl.

2. The compound as claimed in claim 1 wherein Q represents furo[3,2-b]pyridinyl, furo[3,4-b]pyridinyl, furo[3,2-d]pyrimidinyl, furo[3,4-d]pyrimidinyl, thieno[2,3-b]pyridinyl, thieno[3,2-b]pyridinyl, thieno[3,4-b]pyridinyl, thieno[2,3-d]pyrimidinyl, thieno[3,2-d]pyrimidinyl, thieno[3,4-d]pyrimidinyl, pyrrolo[3,2-b]pyridinyl, pyrrolo[3,4-b]pyridinyl, pyrrolo[1,2-a]pyrimidinyl, pyrrolo[3,2-d]pyrimidinyl, pyrrolo[3,4-d]-pyrimidinyl, pyrrolo[1,2-a][1,3,5]triazinyl, pyrazolo[3,4-b]pyridinyl, pyrazolo[4,3-b]pyridinyl, pyrazolo[4,5-b]pyridinyl, pyrazolo[1,5-a]pyrimidinyl, pyrazolo[3,4-d]-pyrimidinyl, pyrazolo[4,3-d]pyrimidinyl, pyrazolo[4,5-d]pyrimidinyl, pyrazolo[1,5-a]-[1,3,5]triazinyl, oxazolo[5,4-b]pyridinyl, oxazolo[5,4-d]pyrimidinyl, isoxazolo[4,3-b]-pyridinyl, isoxazolo[5,4-b]pyridinyl, isoxazolo[4,5-b]pyridinyl, isoxazolo[4,3-d]pyrimidinyl, isoxazolo[4,5-d]pyrimidinyl, isoxazolo[5,4-d]pyrimidinyl, thiazolo[5,4-b]-pyridinyl, thiazolo[5,4-d]pyrimidinyl, isothiazolo[4,3-b]pyridinyl, isothiazolo[4,5-b]-pyridinyl, isothiazolo[5,4-b]pyridinyl, isothiazolo[4,3-d]pyrimidinyl, isothiazolo[4,5-d]-pyrimidinyl, isothiazolo[5,4-d]pyrimidinyl, imidazo[4,5-b]pyridinyl, imidazo[1,5-a]-pyrimidinyl, imidazo[1,5-a][1,3,5]triazinyl, purinyl, [1,2,3]triazolo[1,5-a]pyrimidinyl or [1,2,3]triazolo[1,5-a][1,3,5]triazinyl, any of which groups may be optionally substituted by one, two or three substituents independently selected from halogen, cyano, nitro, $C_{1-6}$ alkyl, trifluoromethyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkyl sulfonyl, amino, $C_{1-6}$ alkyl-amino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, amino-carbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

3. The compound as claimed in claim 1 wherein Q represents a group of formula (Qa), (Qb), (Qc), (Qd), (Qe), (Qf) or (Qg):

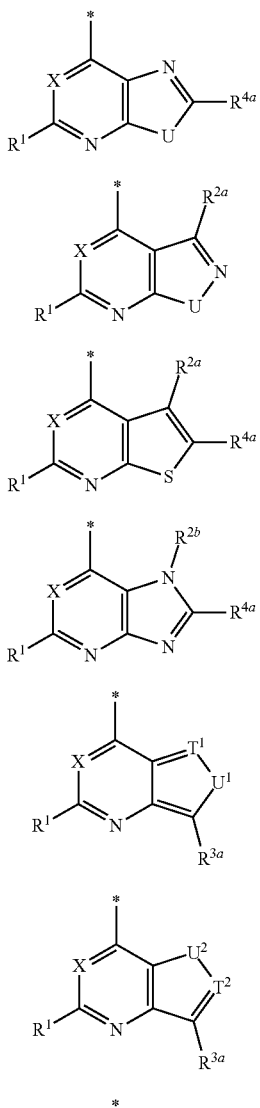

in which the asterisk (*) represents the point of attachment to the remainder of the molecule;

X represents N or CH;
U represents oxygen, sulfur or N—$R^{3b}$;
$U^1$ represents oxygen, sulfur or N—$R^{4b}$;
$U^2$ represents oxygen, sulfur or N—$R^{2b}$;
$T^1$ represents N or C—$R^{2a}$;
$T^2$ represents N or C—$R^{4a}$;
$R^1$ represents hydrogen, halogen, cyano, nitro, $C_{1-6}$ alkyl, trifluoromethyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^{2a}$ represents hydrogen, halogen, cyano, $C_{1-6}$ alkyl, trifluoromethyl, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^{2b}$ represents hydrogen, $C_{1-6}$ alkyl, trifluoromethyl, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^{3a}$ represents hydrogen, halogen, cyano, $C_{1-6}$ alkyl or trifluoromethyl;

$R^{3b}$ represents hydrogen or $C_{1-6}$ alkyl;

$R^{4a}$ represents hydrogen, halogen, cyano, $C_{1-6}$ alkyl, trifluoromethyl, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl; or $R^{4a}$ represents aryl or heteroaryl, either of which groups may be optionally substituted by one or more substituents; and $R^{4b}$ represents hydrogen, $C_{1-6}$ alkyl, trifluoromethyl, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl; or $R^{4b}$ represents aryl or heteroaryl, either of which groups may be optionally substituted by one or more substituents.

4. The compound according to claim 3 represented by formula (IIA), or a pharmaceutically acceptable salt or solvate thereof:

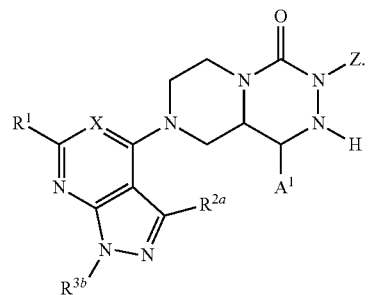

5. The compound as claimed in claim 3 wherein $R^{2a}$ represents hydrogen or $C_{1-6}$ alkyl.

6. The compound as claimed in claim 3 represented by formula (IIB), or a pharmaceutically acceptable salt or solvate thereof:

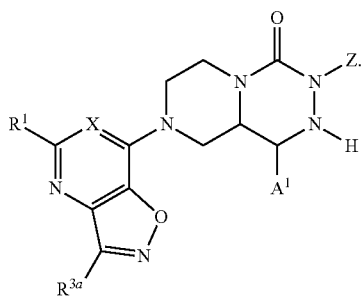

(IIB)

7. The compound as claimed in claim 1 wherein Z represents $C_{1-6}$ alkyl, $C_{3-7}$ cycloalkyl, $C_{3-7}$ cycloalkyl($C_{1-6}$) alkyl, $C_{3-7}$ heterocycloalkyl, $C_{3-7}$ heterocycloalkyl($C_{1-6}$) alkyl, aryl, aryl($C_{1-6}$)alkyl, heteroaryl or heteroaryl($C_{1-6}$) alkyl, any of which groups may be optionally substituted by one, two or three substituents independently selected from halogen, cyano, nitro, $C_{1-6}$ alkyl, trifluoromethyl, cyano-($C_{1-6}$)alkyl, ($C_{3-7}$)heterocycloalkyl, halo($C_{3-7}$)heterocycloalkyl, ($C_{1-6}$)alkyl($C_{3-7}$)-heterocycloalkyl, ($C_{2-6}$)alkoxycarbonyl($C_{3-7}$)heterocycloalkyl, dihalo($C_{3-7}$)-heterocycloalkyl, ($C_{3-7}$)heterocycloalkyl($C_{1-6}$)alkyl, ($C_{1-6}$)alkyl ($C_{3-7}$)heterocycloalkyl-($C_{1-6}$)alkyl, heteroaryl, hydroxy, oxo, $C_{1-6}$ alkoxy, difluoromethoxy, trifluoromethoxy, trifluoroethoxy ($C_{3-7}$)heterocycloalkoxy, ($C_{2-6}$)alkoxycarbonyl ($C_{3-7}$)heterocycloalkoxy, ($C_{3-7}$)heterocycloalkyl($C_{1-6}$) alkoxy, aryloxy, haloaryloxy, ($C_{1-6}$)alkoxyaryloxy, $C_{1-3}$ alkylenedioxy, dihalo($C_{1-3}$)alkylenedioxy, arylcarbonyloxy, $C_{1-6}$ alkylthio, $C_{1-6}$ alkylsulfinyl, $C_{1-6}$ alkyl sulfonyl, amino, $C_{1-6}$ alkylamino, di($C_{1-6}$)alkylamino, di($C_{1-6}$)alkylamino ($C_{1-6}$)alkyl, arylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aryloxycarbonyl, amino-carbonyl, $C_{1-6}$ alkylaminocarbonyl, di($C_{1-6}$) alkylaminocarbonyl, aminosulfonyl, $C_{1-6}$ alkylaminosulfonyl and di($C_{1-6}$)alkylaminosulfonyl.

8. The compound as claimed in claim 7 wherein Z represents aryl or heteroaryl, either of which groups may be optionally substituted by one, two or three substituents independently selected from $C_{1-6}$ alkyl, trifluoromethyl, $C_{1-6}$ alkoxy and trifluoromethoxy.

9. The compound as claimed in claim 1 wherein $A^1$ represents hydrogen or $C_{1-6}$ alkyl.

10. The compound as claimed in claim 3 wherein $R^1$ represents hydrogen or amino.

11. The compound of formula (I) as defined in claim 1 selected from,
    8-(6-Amino-1-methylpyrazolo[3,4-d]pyrimidin-4-yl)-3-(4-methoxyphenyl)-1,2,6,7,9,9a-hexahydropyrazino[1,2-d][1,2,4]triazin-4-one,
    8-(6-Amino-1-methylpyrazolo[3,4-d]pyrimidin-4-yl)-3-(4-methoxy-3-methylphenyl)-1,2,6,7,9,9a-hexahydropyrazino[1,2-d][1,2,4]triazin-4-one,
    (9aS)-8-(6-Amino-1-methyl-1H-pyrazolo[3,4-d]pyrimidin-4-yl)-3-(4-methoxy-3-methyl-phenyl)-1,2,6,7,9,9a-hexahydropyrazino[1,2-d][1,2,4]triazin-4-one,
    (9aS)-8-(6-Amino-1-methyl-1H-pyrazolo[3,4-d]pyrimidin-4-yl)-3-(4-methoxy-3-methyl-phenyl)-6,7,9,9a-tetrahydropyrazino[1,2-d][1,2,4]triazin-4-one,
    8-(6-Amino-1,3-dimethylpyrazolo[3,4-d]pyrimidin-4-yl)-3-(4-methoxy-3-methylphenyl)-1,2,6,7,9,9a-hexahydropyrazino[1,2-d][1,2,4]triazin-4-one,
    (9aS)-8-(6-Amino-1,3-dimethylpyrazolo[3,4-d]pyrimidin-4-yl)-3-(4-methoxy-3-methyl-phenyl)-1,2,6,7,9,9a-hexahydropyrazino[1,2-d][1,2,4]triazin-4-one,
    8-(6-Amino-1-methyl-1H-pyrazolo[3,4-d]pyrimidin-4-yl)-3-[5-methoxy-6-(trifluoro-methyl)pyridin-2-yl]-1,2,6,7,9,9a-hexahydropyrazino[1,2-d][1,2,4]triazin-4-one,
    (9aS)-8-(6-Amino-1-methyl-1H-pyrazolo[3,4-d]pyrimidin-4-yl)-3-[4-(trifluoromethoxy)-phenyl]-1,2,6,7,9,9a-hexahydropyrazino[1,2-d][1,2,4]triazin-4-one,
    cis- and trans-8-(6-Amino-1-methyl-1H-pyrazolo[3,4-d]pyrimidin-4-yl)-3-(4-methoxy-3-methylphenyl)-1-methyl-1,2,6,7,9,9a-hexahydropyrazino[1,2-d][1,2,4]triazin-4-one,
    (9aS)-3-(4-Methoxy-3-methylphenyl)-8-(1-methyl-1H-pyrazolo[3,4-b]pyridin-4-yl)-1,2,6,7,9,9a-hexahydropyrazino[1,2-d][1,2,4]triazin-4-one, and
    (9aS)-8-(5-Amino-3-methylisoxazolo[4,5-d]pyrimidin-7-yl)-3-(4-methoxy-3-methyl-phenyl)-1,2,6,7,9,9a-hexahydropyrazino[1,2-d][1,2,4]triazin-4-one.

12. A pharmaceutical composition comprising a compound of formula (I) as defined in claim 1 or an N-oxide thereof, or a pharmaceutically acceptable salt or solvate thereof, in association with a pharmaceutically acceptable carrier.

13. A method for the treatment of a disease or condition mediated by PI4KIIIβ selected from an inflammatory, autoimmune or oncological disorder, a viral disease or malaria, and organ or cell transplant rejection, which comprises administering to a patient in need of such treatment an effective amount of a compound of formula (I) as defined in claim 1 or an N-oxide thereof, or a pharmaceutically acceptable salt or solvate thereof.

14. The compound as claimed in claim 4 wherein $R^{2a}$ represents hydrogen or $C_{1-6}$ alkyl.

15. The compound as claimed in claim 4 wherein Z represents $C_{1-6}$ alkyl, $C_{3-7}$ cycloalkyl, $C_{3-7}$ cycloalkyl($C_{1-6}$) alkyl, $C_{3-7}$ heterocycloalkyl, $C_{3-7}$ heterocycloalkyl($C_{1-6}$) alkyl, aryl, aryl($C_{1-6}$)alkyl, heteroaryl or heteroaryl($C_{1-6}$) alkyl, any of which groups may be optionally substituted by one, two or three substituents independently selected from halogen, cyano, nitro, $C_{1-6}$ alkyl, trifluoromethyl, cyano-($C_{1-6}$)alkyl, ($C_{3-7}$)heterocycloalkyl, halo($C_{3-7}$)heterocycloalkyl, ($C_{1-6}$)alkyl($C_{3-7}$)-heterocycloalkyl, ($C_{2-6}$)alkoxycarbonyl($C_{3-7}$)heterocycloalkyl, dihalo($C_{3-7}$)-heterocycloalkyl, ($C_{3-7}$)heterocycloalkyl($C_{1-6}$)alkyl, ($C_{1-6}$)alkyl ($C_{3-7}$)heterocycloalkyl-($C_{1-6}$)alkyl, heteroaryl, hydroxy, oxo, $C_{1-6}$ alkoxy, difluoromethoxy, trifluoromethoxy, trifluoroethoxy ($C_{3-7}$)heterocycloalkoxy, ($C_{2-6}$)alkoxycarbonyl ($C_{3-7}$)heterocycloalkoxy, ($C_{3-7}$)heterocycloalkyl($C_{1-6}$) alkoxy, aryloxy, haloaryloxy, ($C_{1-6}$)alkoxyaryloxy, $C_{1-3}$ alkylenedioxy, dihalo($C_{1-3}$)alkylenedioxy, arylcarbonyloxy, $C_{1-6}$ alkylthio, $C_{1-6}$ alkylsulfinyl, $C_{1-6}$ alkyl sulfonyl, amino, $C_{1-6}$ alkylamino, di($C_{1-6}$)alkylamino, di($C_{1-6}$)alkylamino ($C_{1-6}$)alkyl, arylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aryloxycarbonyl, amino-carbonyl, $C_{1-6}$ alkylaminocarbonyl, di($C_{1-6}$) alkylaminocarbonyl, aminosulfonyl, $C_{1-6}$ alkylaminosulfonyl and di($C_{1-6}$)alkylaminosulfonyl.

16. The compound as claimed in claim 6 wherein Z represents $C_{1-6}$ alkyl, $C_{3-7}$ cycloalkyl, $C_{3-7}$ cycloalkyl($C_{1-6}$) alkyl, $C_{3-7}$ heterocycloalkyl, $C_{3-7}$ heterocycloalkyl($C_{1-6}$) alkyl, aryl, aryl($C_{1-6}$)alkyl, heteroaryl or heteroaryl($C_{1-6}$) alkyl, any of which groups may be optionally substituted by one, two or three substituents independently selected from halogen, cyano, nitro, $C_{1-6}$ alkyl, trifluoromethyl, cyano-$(C_{1-6})$alkyl, $(C_{3-7})$heterocycloalkyl, halo$(C_{3-7})$heterocycloalkyl, $(C_{1-6})$alkyl$(C_{3-7})$-heterocycloalkyl, $(C_{2-6})$alkoxycarbonyl$(C_{3-7})$heterocycloalkyl, dihalo$(C_{3-7})$-heterocycloalkyl, $(C_{3-7})$heterocycloalkyl$(C_{1-6})$alkyl, $(C_{1-6})$alkyl $(C_{3-7})$heterocycloalkyl-$(C_{1-6})$alkyl, heteroaryl, hydroxy, oxo, $C_{1-6}$ alkoxy, difluoromethoxy, trifluoromethoxy, trifluoroethoxy $(C_{3-7})$heterocycloalkoxy, $(C_{2-6})$alkoxycarbonyl $(C_{3-7})$heterocycloalkoxy, $(C_{3-7})$heterocycloalkyl$(C_{1-6})$alkoxy, aryloxy, haloaryloxy, $(C_{1-6})$alkoxyaryloxy, $C_{1-3}$ alkylenedioxy, dihalo$(C_{1-3})$alkylenedioxy, arylcarbonyloxy, $C_{1-6}$ alkylthio, $C_{1-6}$ alkylsulfinyl, $C_{1-6}$ alkyl sulfonyl, amino, $C_{1-6}$ alkylamino, di$(C_{1-6})$alkylamino, di$(C_{1-6})$alkylamino $(C_{1-6})$alkyl, arylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aryloxycarbonyl, amino-carbonyl, $C_{1-6}$ alkylaminocarbonyl, di$(C_{1-6})$alkylaminocarbonyl, aminosulfonyl, $C_{1-6}$ alkylaminosulfonyl and di$(C_{1-6})$alkylaminosulfonyl.

17. The compound as claimed in claim 15 wherein Z represents aryl or heteroaryl, either of which groups may be optionally substituted by one, two or three substituents independently selected from $C_{1-6}$ alkyl, trifluoromethyl, $C_{1-6}$ alkoxy and trifluoromethoxy.

18. The compound as claimed in claim 16 wherein Z represents aryl or heteroaryl, either of which groups may be optionally substituted by one, two or three substituents independently selected from $C_{1-6}$ alkyl, trifluoromethyl, $C_{1-6}$ alkoxy and trifluoromethoxy.

19. The compound as claimed in claim 15 wherein $A^1$ represents hydrogen or $C_{1-6}$ alkyl.

20. The compound as claimed in claim 15 wherein $R^1$ represents hydrogen or amino.

* * * * *